(12) United States Patent
Seibel et al.

(10) Patent No.: US 11,883,132 B2
(45) Date of Patent: Jan. 30, 2024

(54) SYSTEM AND METHOD FOR RANKING BACTERIAL ACTIVITY LEADING TO TOOTH AND GUM DISEASE

(71) Applicant: University of Washington, Seattle, WA (US)

(72) Inventors: Eric J. Seibel, Seattle, WA (US); Yuanzheng Gong, Seattle, WA (US); Zheng Xu, Seattle, WA (US); Jeffrey S. McLean, Seattle, WA (US); Yaxuan Zhou, Seattle, WA (US)

(73) Assignee: University of Washington, Seattle, WA (US)

( * ) Notice: Subject to any disclaimer, the term of this patent is extended or adjusted under 35 U.S.C. 154(b) by 1108 days.

(21) Appl. No.: 16/344,728

(22) PCT Filed: Oct. 27, 2017

(86) PCT No.: PCT/US2017/058869
§ 371 (c)(1),
(2) Date: Apr. 24, 2019

(87) PCT Pub. No.: WO2018/081637
PCT Pub. Date: May 3, 2018

(65) Prior Publication Data
US 2019/0328234 A1 Oct. 31, 2019

Related U.S. Application Data

(60) Provisional application No. 62/414,581, filed on Oct. 28, 2016.

(51) Int. Cl.
*A61B 5/145* (2006.01)
*A61B 5/00* (2006.01)
(Continued)

(52) U.S. Cl.
CPC .......... *A61B 5/0088* (2013.01); *A61B 5/0071* (2013.01); *A61B 5/14539* (2013.01);
(Continued)

(58) Field of Classification Search
CPC ................ A61B 5/0071; A61B 5/0059; A61B 2562/0238; A61B 5/0088; A61B 5/4547;
(Continued)

(56) References Cited

U.S. PATENT DOCUMENTS 4,479,449 A 10/1984 Alfano
RE31,815 E 1/1985 Alfano
(Continued)

FOREIGN PATENT DOCUMENTS

| JP | 2001-068861 A | 3/2001 |
| JP | 2002-269548 A | 9/2002 |
| WO | 2014/113017 A1 | 7/2014 |

OTHER PUBLICATIONS

RS Jones et al., "Near-Infrared Transillumination at 1310-nm for the Imaging of Early Dental Decay," Optics Express, 11(18):2259-2265 (2003).
(Continued)

*Primary Examiner* — Deborah L Malamud
(74) *Attorney, Agent, or Firm* — Christensen O'Connor Johnson Kindness PLLC

(57) ABSTRACT

A system for the optical measurement of pH includes a light emitter to emit an excitation light, and a detector coupled to receive florescence light produced by a compound in a mouth of a patient in response to the excitation light. A controller is coupled to the detector, and the controller includes logic that when executed by the controller, causes the system to perform operations. The operations may include emitting the excitation light from the light emitter; measuring an intensity of the florescence light emitted from
(Continued)

a surface of individual teeth in a plurality of teeth in the mouth; and determining, based on the intensity of the florescence light, one or more locations on the individual teeth likely to develop demineralization.

23 Claims, 13 Drawing Sheets

(51) Int. Cl.
    *A61C 19/06* (2006.01)
    *A61K 49/00* (2006.01)

(52) U.S. Cl.
    CPC .......... *A61B 5/7264* (2013.01); *A61C 19/063* (2013.01); *A61K 49/0017* (2013.01)

(58) Field of Classification Search
    CPC ...... A61B 2562/0233; A61B 2562/146; A61B 5/682; A61B 1/24; A61N 2005/0651; A61C 9/0053; A61Q 11/00
    See application file for complete search history.

(56) References Cited

U.S. PATENT DOCUMENTS

| | | |
|---|---|---|
| 4,515,476 A | 5/1985 | Ingmar |
| 4,839,158 A | 6/1989 | Michaels |
| 5,345,941 A | 9/1994 | Rava et al. |
| 5,382,163 A | 1/1995 | Putnam |
| 5,413,108 A | 5/1995 | Alfano |
| 5,450,293 A | 9/1995 | Hoffman |
| 5,483,951 A | 1/1996 | Frassica et al. |
| 5,816,676 A | 10/1998 | Meyers et al. |
| 6,024,562 A | 2/2000 | Hibst et al. |
| 6,186,780 B1 | 2/2001 | Hibst et al. |
| 6,231,338 B1 | 5/2001 | de Josselin de Jong et al. |
| 6,294,775 B1 | 9/2001 | Seibel et al. |
| 6,563,105 B2 | 5/2003 | Seibel et al. |
| 6,584,341 B1 | 6/2003 | Mandelis et al. |
| 6,615,068 B1 | 9/2003 | Alfano et al. |
| 6,821,116 B2 | 11/2004 | Severance |
| 6,975,898 B2 | 12/2005 | Seibel |
| 7,319,529 B2 | 1/2008 | Babayoff |
| 7,475,821 B2 | 1/2009 | Barkan et al. |
| 7,766,658 B2 | 8/2010 | Tricca et al. |
| 7,796,243 B2 | 9/2010 | Choo-Smith et al. |
| 7,942,814 B2 | 5/2011 | Remijan et al. |
| 7,955,076 B2 | 6/2011 | Yamagishi |
| 8,027,709 B2 | 9/2011 | Amone et al. |
| 8,182,479 B2 | 5/2012 | Schneider |
| 8,184,147 B2 | 5/2012 | Crucs et al. |
| 8,224,045 B2 | 7/2012 | Burns et al. |
| 8,285,039 B2 | 10/2012 | Komiya |
| 8,371,848 B2 | 2/2013 | Okawa et al. |
| 8,466,210 B2 | 6/2013 | Zech et al. |
| 8,556,625 B2 | 10/2013 | Lovely |
| 8,992,216 B2 | 3/2015 | Karazivan |
| 9,042,967 B2 * | 5/2015 | Dacosta .................. A61B 5/445 600/476 |
| 9,060,690 B2 | 6/2015 | Liang et al. |
| 10,080,484 B2 | 9/2018 | Yang et al. |
| 2003/0040009 A1 | 2/2003 | Denny et al. |
| 2004/0141960 A1 | 7/2004 | Häberlein et al. |
| 2004/0220498 A1 | 11/2004 | Li et al. |
| 2004/0240716 A1 | 12/2004 | de Josselin de Jong et al. |
| 2005/0202363 A1 | 9/2005 | Osterwalder |
| 2005/0221401 A1 | 10/2005 | Nomura et al. |
| 2006/0263825 A1 | 11/2006 | Denny et al. |
| 2007/0134615 A1 | 6/2007 | Lovely |
| 2008/0248447 A1 | 10/2008 | Karazivan |
| 2009/0055024 A1 | 2/2009 | Kay |
| 2010/0279248 A1 | 11/2010 | Mourad et al. |
| 2011/0090513 A1 | 4/2011 | Seidl et al. |
| 2011/0117025 A1 | 5/2011 | Dacosta et al. |
| 2012/0326055 A1 | 12/2012 | Wilson et al. |
| 2013/0122468 A1 | 5/2013 | Abrams et al. |
| 2013/0323674 A1 | 12/2013 | Hakomori et al. |
| 2014/0124682 A1 | 5/2014 | Lampalzer |
| 2014/0199649 A1 | 7/2014 | Apte et al. |
| 2015/0005596 A1 | 1/2015 | Wilzbach |
| 2015/0010878 A1 | 1/2015 | Seibel et al. |
| 2015/0038350 A1 | 2/2015 | Nishinaga et al. |
| 2015/0164335 A1 | 6/2015 | Van Der Poel et al. |
| 2015/0216398 A1 | 8/2015 | Yang et al. |

OTHER PUBLICATIONS

RO Rocha et al., "In Vivo Effectiveness of Laser Fluorescence Compared to Visual Inspection and Radiography for the Detection of Occlusal Caries in Primary Teeth," Caries Research, 37(6):437-441 (2003).
JD Bader et al., "A Systematic Review of the Performance of a Laser Fluorescence Device for Detecting Caries," Journal of the American Dental Association, 135(10):1413-1426 (2004).
K Carter et al., "Automated Quantification of Dental Plaque Accumulation Using Digital Imaging," Journal of Dentistry, 32(8):623-628 (2004).
PR Gomes et al., "Dental Caries in Paulinia, Sao Paulo State, Brazil, and WHO Goals for 2000 and 2010," Cad Saude Publica, 20(3):866-870 (2004).
GC Jones et al., "Transillumination of Interproximal Caries Lesions with 830-nm Light," Lasers in Dentistry X, 5313:17-22 (2004).
RS Jones et al., "Imaging Artificial Caries Under Composite Sealants and Restorations," Journal of Biomedical Optics, 9(6):1297-1304 (2004).
CM Bühler et al., "Imaging of Occlusal Dental Caries (Decay) with Near-IR Light at 1310-nm," Optics Express, 13(2):573-582 (2005).
D Fried et al., "Early Caries Imaging and Monitoring With Near-Infrared Light," Dental Clinics of North America, 49(4):771-793 (2005).
JC Hamilton "Should a Dental Explorer Be Used to Probe Suspected Lesions?" Journal of the American Dental Association, 136(11):1526-1532 (2005).
RS Jones et al., "The Effect of High-Index Liquids on PS-OCT Imaging of Dental Caries," Lasers in Dentistry XI, 5687:34-41 (2005).
P Ngaotheppitak et al., "Measurement of the Severity of Natural Smooth Surface (Interproximal) Caries Lesions with Polarization Sensitive Optical Coherence Tomography," Lasers in Surgery and Medicine, 37(1):78-88 (2005).
CM Brown et al., "Optomechanical Design and Analysis For a Scanning Fiber Endoscope," Proceedings of the 2001 ASME International Mechanical Engineering Congress and Exposition, 51:165-166 (2006).
CL Darling et al., "Light Scattering Properties of Natural and Artificially Demineralized Dental Enamel at 1310 nm," Journal of Biomedical Optics, 11(3):034023 (2006).
EK Delgado-Angulo et al., "Influence of Host Related Indicators on Dental Caries in the Permanent Dentition," Acta Odontal Latinoam, 19(2):85-92 (2006).
RS Jones et al., "Remineralization of Enamel Caries Can Decrease Optical Reflectivity," Journal of Dental Research, 85(9):804-808 (2006).
RS Jones et al., "Imaging Artificial Caries on the Occlusal Surfaces With Polarization-Sensitive Optical Coherence Tomography," Caries Research, 40(2):81-89 (2006).
RS Jones et al., "Remineralization of In Vitro Dental Caries Assessed With Polarization-Sensitive Optical Coherence Tomography," Journal of Biomedical Optics, 11(1):014016-1-9 (2006).
P Ngaotheppitak et al., "PS-OCT of Occlusal and Interproximal Caries Lesions Viewed From Occlusal Surfaces," Lasers in Dentistry X, 6137:61370L-1-8 (2006).
T Ai et al., "Risk Indicators For Childhood Caries in Taiwan," Community Dentistry and Oral Epidemiology, 34(6):437-445 (2006).
AF Zandona et al., "Diagnostic Tools for Early Caries Detection," Journal of the American Dental Association, 137(12):1675-1684 (2006).

(56) References Cited

OTHER PUBLICATIONS

SL Chong et al., "Nondestructive Measurement of the Inhibition of Demineralization on Smooth Surfaces Using Polarization-Sensitive Optical Coherence Tomography," Lasers in Surgery and Medicine, 39(5):422-427 (2007).
M Du et al., "Caries in Preschool Children and Its Risk Factor in 2 Provinces in China," Quintessence International, 38(2):143-151 (2007).
D Fried et al., "Polarization Sensitive Optical Coherence Tomography for Quantifying the Severity of Natural Caries Lesions on Occlusal Surfaces," Lasers in Dentistry XIII, 6425:64250U-1-8 (2007).
JS Greenspan et al., "A Global Theme—Poverty and Human Development," Journal of Dental Research, 86(10):917-918 (2007).
S Naidoo et al., "Nutrition, Oral Health and the Young Child," Maternal and Child Nutrition, 3(4):312-321 (2007).
HD Sgan-Cohen et al., "Health, Oral Health and Poverty," Journal of the American Dental Association, 138(11):1437-1442 (2007).
E Barberia et al., "A Clinical Study of Caries Diagnosis With a Laser Fluorescence System," Journal of the American Dental Association, 139(5):572-579 (2008).
K Hirasuna et al., "Near-Infrared Imaging of Developmental Defects in Dental Enamel," Journal of Biomedical Optics, 13(4):044011-1-7 (2008).
JA Rodrigues et al., "The Influence of Zero-Value Subtraction on the Performance of Two Laser Fluorescence Devices for Detecting Occlusal Caries in Vivo," Journal of the American Dental Association, 139(8):1105-1112 (2008).
B Valera et al., "Comparison of Visual Inspection, Radiographic Examination, Laser Fluorescence and Their Combinations on Treatment Decisions for Occlusal Surfaces," American Journal of Dentistry, 21(1):25-29 (2008).
L Coulthwaite et al., "Evaluation of in Vivo Denture Plaque Assessment Methods," British Dental Journal, 207(6):E12, 6 pages (2009).
L Coulthwaite et al., "QLF is Not Readily Suitable for in Vivo Denture Plaque Assessment," Journal of Dentistry, 37(11):898-901 (2009).
JD Featherstone., "Remineralization, the Natural Caries Repair Process—the Need for New Approaches," Advances in Dental Research, 21(1):4-7 (2009).
Le Kagihara et al., "Assessment, Management, and Prevention of Early Childhood Caries," Journal of the American Academy of Nurse Practitioners, 21(1):1-10 (2009).
C Lee et al., "Non-Destructive Measurement of Demineralization and Remineralization in the Occlusal Pits and Fissures of Extracted 3rd Molars with PS-OCT," Lasers in Dentistry XV, 7162:71620V-1-6 (2009).
C Lee et al., "Polarization-Sensitive Optical Coherence Tomographic Imaging of Artificial Demineralization on Exposed Surfaces of Tooth Roots," Dental Materials, 25(6):721-728 (2009).
D Lee et al., "Near-IR Multi-Modal Imaging of Natural Occlusal Lesions," Lasers in Dentistry XV, 7162:71620X-1-7 (2009).
CH Silva-Lovato et al., "Evaluation of a Computerized Method for Denture Biofilm Quantification: Inter-Examiner Reproducibility," Journal of Prosthodontics, 18(4):332-336 (2009).
SK Manesh et al., "Nondestructive Assessment of Dentin Demineralization Using Polarization-Sensitive Optical Coherence Tomography After Exposure to Fluoride and Laser Irradiation," Journal of Biomedical Materials Research B: Applied Biomaterials, 90(2):802-812 (2009).
SK Manesh et al., "Polarization-Sensitive Optical Coherence Tomography for the Nondestructive Assessment of the Remineralization of Dentin," Journal of Biomedical Optics, 14(4):044002-1-6 (2009).
SM Douglas et al., "Imaging Natural Occlusal Caries Lesions With Optical Coherence Tomography," Lasers in Dentistry XVI, 7549:75490N-1-7 (2010).
D Fried., "Lasers and Optics Measuring Tooth Decay," Optics & Photonics News, pp. 15-19 (2010).
C Lee et al., "In Vitro Near-Infrared Imaging of Occlusal Dental Caries Using a Germanium-Enhanced CMOS Camera," Lasers in Dentistry XVI, 7549:75490K-1-7 (2010).
C Lee et al., "Nondestructive Assessment of the Severity of Occlusal Caries Lesions With Near-Infrared Imaging at 1310 NM," Journal of Biomedical Optics, 15(4):047011-1-7 (2010).
CM Lee et al., "Wide Field Fluorescence Imaging in Narrow Passageways Using Scanning Fiber Endoscope Technology," Endoscopic Microscopy V, Proceedings of SPIE, 7558:755806-1-10 (2010).
T Louie et al., "Clinical Assessment of Early Tooth Demineralization Using Polarization Sensitive Optical Coherence Tomography," Lasers in Surgery and Medicine, 42(10):738-745 (2010).
M Staninec et al., "In Vivo Near-IR Imaging of Approximal Dental Decay at 1,310 NM," Lasers in Surgery and Medicine, 42(4):292-298 (2010).
MAB Blank et al., "Laser Scanning Dental Probe For Endodontic Root Canal Treatment," Lasers in Dentistry XVII, Proceedings of SPIE 2011, 7884:788403-1-7 (2011).
CK Hope et al., "Photobleaching of Red Fluorescence in Oral Biofilms," Journal of Periodontal Research, 46(2):228-234 (2011).
International Search Report and Written Opinion from the International Searching Authority dated Jan. 4, 2018 for International Application No. PCT/US2017/058869, filed Oct. 27, 2017, 10 pages.
International Preliminary Report on Patentability dated May 9, 2019 for International Application No. PCT/US2017/058869, filed Oct. 27, 2017, 9 pages.
Agarwal, N. 2013. MS Thesis, Dept. of Bioengineering, University of Washington, "Quantification of DNA Content using Optical Projection Tomographic Microscopy for Early Cancer Diagnosis."
Agarwal, N., A.M. Biancardi, F.W. Patten, A.P. Reeves, and E.J. Seibel. 2014. "Three-dimensional dna image cytometry by optical projection tomographic microscopy for early cancer diagnosis." Journal of Medical Imaging 1(1):1-10, paper 017501.
Chou, K.F., Q. Miao, R.L. Coe, and E.J. Seibel. 2012 (online publication). "3D imaging of fine needle aspirates using optical projection tomographic microscopy," Journal of Cytology and Histology. doi:10.4172/2157-7099.S2-001.
Chung C, Dew K, Cole A, Zia J, Fogarty J, Kientz JA, Munson SA. 2016. "Boundary Negotiating Artifacts in Personal Informatics: Patient-Provider Collaboration with Patient-Generated Data." Proceedings of CSCW 2016. DOI: http://dx.doi.org/10.1145/2818048.2819926.
Chung C, Cook J, Bales E, Zia J, Munson SA. 2015. "More Than Telemonitoring: Health Provider Use and Nonuse of Life-Log Data in Irritable Bowel Syndrome and Weight Management." Journal of Medical Internet Research 2015; 17(8). DOI: 10.2196/jmir.4364.
Clawson J, Pater JA, Miller AD, Mamykina L, Mynatt ED. 2015. No Longer Wearing: Investigating the Abandonment of Personal Health-Tracking Technologies on Craigslist. Proceedings of the 2015 ACM International Joint conference on Pervasive and Ubiquitous Computing (UbiComp '15).
Coe, R.L. 2013. PhD Dissertation, Dept. of Bioengineering, University of Washington, "Computational Modeling of Optical Projection Tomographic Microscopy."
Cordeiro, F., Epstein, D.A., Thomaz, E., Bales, E., Jagannathan, A.K., Abowd, G.D., and Fogarty, J. 2015. "Barriers and Negative Nudges: Exploring Challenges in Food Journaling." Proceedings of CHI 2015, 1159-1162.
De Greef, L., Goel, M., Seo, M.J., Larson, E.C., Stout, J.W., Taylor, J.A., Patel, S.N. 2014. "Bilicam: using mobile phones to monitor newborn jaundice." In the Proceedings of UbiComp 2014, pp. 331-342. (Best Paper Award Honorable Mention).
Drabold, Will. 2016. "Dentists lobby is blocking route to low-cost care," The Seattle Times, pages A1 & A4, Jan. 4, 2016.
Edlund, A., Y. Yang, A. P. Hall, L. Gou, R. Lux, X. He, K. E. Nelson, K. H. Nealson, S. Yooseph, W. Shi and J. S. McLean. 2013. "A novel in vitro biofilm model maintaining a high species and metabolic diversity similar to the human oral microbiome." Microbiome 1(25): doi:10.1186/2049-2618-1181-1125.
Fauver, M.L., E.J. Seibel, J.R. Rahn, M.G. Meyer, F.W. Patten, T. Neumann, and A.C. Nelson. 2005. "Three-dimensional imaging of

(56) References Cited

OTHER PUBLICATIONS single isolated cell nuclei using optical projection tomography." OSA Optics Express 13(11):4210-4223.

Fritz, T., Huang, E.M., Murphy, G.C., and Zimmermann, T. 2014. "Persuasive Technology in the Real World : A Study of Long-Term Use of Activity Sensing Devices for Fitness." Proceedings of CHI 2014, 487-496. DOI: 10.1145/2556288.2557383.

Gimenez, T, Braga, MM, Raggio, DP, Deery, C, Ricketts, DN, Mendes, FM. 2013. "Fluorescence-Based Methods for Detecting Caries Lesions: Systematic Review, Meta-Analysis and Sources of Heterogeneity," PLOS ONE, Apr. 4, 2013, DOI: 10.1371/journal. pone.0060421.

Gong, Y., D. Hu, B. Hannaford, and E.J. Seibel. 2014. "Accurate 3D virtual reconstruction of surgical field using calibrated trajectories of an image-guided medical robot." Journal Medical Imaging 1(3):035002.

Gong, Y., D. Meng, and E.J. Seibel. 2015. "Bound constrained bundle adjustment for reliable 3D reconstruction." Optics Express 23(8):10771-10785.

Han, J. and Burgess, K. 2010. "Fluorescent indicators for intracellular pH," Chemical Reviews 110(5): 2709-2728.

Centers for Disease Control and Prevention (CDC). 2014. "Hygiene-Related Diseases: Dental Caries (Tooth Decay)." Atlanta: CDC. http://www.cdc.gov/healthywater/hygiene/disease/dental_caries. html.

Inglis, SC, Clark, RA, McAlister, FA, Cleland, JG. 2011. "Which components of heart failure programmes are effective? A systematic review and meta-analysis of the outcomes of structured telephone support or telemonitoring as the primary component of chronic heart failure management." Journal of Cardiac Failure 13:1028-1040.

Karkar R., Zia J., Vilardaga R, Mishra SR, Fogarty J, Munson SA, Kientz JA. (In press). "A framework for self-experimentation in personalized health." Journal of the American Medical Informatics Association. DOI: http://dx.doi.org/10.1093/jamia/ocv150.

Kassebaum, NJ, Bernabe, E, Dahiya, M, Bhandari, B, Murray, CJL, Marcenes, W. 2015. "Global Burden of Untreated Caries: A Systematic Review and Metaregression," Journal of Dental Research 1-9, DOI: 10.1177/0022034515573272.

Konig, K, Flemming, G, and Hibst, R. 1998. "Laser-induced autofluorescence spectroscopy of dental caries," Cellular and Molecular Biology 44(8):1293-1300.

Larson, E.C., Lee, T., Liu, S., Rosenfeld, M., Patel, S.N. 2011. "Accurate and Privacy Preserving Cough Sensing using a Low-Cost Microphone." In the Proceedings of Ubicomp 2011.

Larson, E.C., Goel, M., Borriello, G., Heltshe, S., Rosenfeld, M., Patel, S.N. 2012. "SpiroSmart: Using a Microphone to Measure Lung Function on a Mobile Phone." In the Proceedings of Ubicomp 2012. (Best Paper Honorable Mention).

Larson, E.C., Goel, M., Redfield, M., Borriello, G., Rosenfeld, M., Patel, S.N. 2013. "Tracking lung function on any phone." In the Proceedings of ACM DEV 2013.

Lazar A, Koehler X, Tanenbaum J, Nguyen D. 2015. "Why We Use and Abandon Smart Devices." Proceedings of the 2015 ACM international Joint conference on Pervasive and Ubiquitous Computing (UbiComp '15).

Lee, C.M., C. Engelbrecht, T.D. Soper, F.C. Helmchen, and E.J. Seibel. 2010. "Scanning fiber endoscopy with highly flexible, 1-mm catheterscopes for wide-field, full-color imaging." Journal of Biophotonics 3(5-6): 385-407.

Lewis J.R., Sauro J. 2009. "The factor structure of the system usability scale." Human Centered Design. Springer Berlin Heidelberg, 94-103.

Luo, J. and O. Gwun. 2009. "A comparison of SIFT, PCA-SIFT and SURF." International Journal of Image Processing 3(4):143-152.

Matvienko, A, Jeon, J, Mandelis, A, Arvizu, G, Gomez, AE, Abrams, SH and Amaechi, BT. 2008. "Dental biothermophotonics: A quantitative photothermal analysis of early dental demineralization," Eur. Phys. J. Special Topics 153, 463-5.

Nørgaard M, Hornbæk K. 2006. "What do usability evaluators do in practice?: an explorative study of think-aloud testing." Proceedings of the 6th conference on Designing Interactive systems (DIS '06), 209-218. DOI=http://dx.doi.org/10.1145/1142405.1142439.

Park S. Y., Chen Y. 2015. "Individual and Social Recognition: Challenges and Opportunities in Migraine Management." Proceedings of the 18th ACM Conference on Computer Supported Cooperative Work & Social Computing (CSCW 15), 1540-1551. DOI: http://dx.doi.org/10.1145/2675133.2675248.

Persson, A., P. Lingstrom, T. Backlund and J. W. van Dijken. 2004. "Evaluation of a skin reference electrode used for intraoral pH measurements in combination with a microtouch electrode." Clin Oral Investig 8(3): 172-175.

Rechmann, P, Charland, D, Rechmann, BMT, and Featherstone, JDB. 2012. "Performance of laser fluorescence devices and visual examination for the detection of occlusal caries in permanent molars," Journal of Biomedical Optics, 17(3): paper 036006.

Rooksby, J., Rost, M., Morrison, A., and Chalmers, M. 2014. "Personal Tracking as Lived Informatics." Proceedings of CHI 2014, 1163-1172. DOI: 10.1145/2556288.2557039.

Sauro J. 2011. "Measuring Usability with The System Usability Scale (Sus)," Measuring U, http://www.measuringu.com/sus.php.

Schlafer, S., J. E. Garcia, M. Greve, M. K. Raarup, B. Nyvad and I. Dige. 2015. "Ratiometric imaging of extracellular pH in bacterial biofilms with C-SNARF-4." Appl Environ Microbiol 81(4): 1267-1273.

Szeliski, R. 2010. "Computer vision: algorithms and applications." Springer Science & Business Media.

Tian, Y., X. He, M. Torralba, S. Yooseph, K. E. Nelson, R. Lux, J. S. McLean, G. Yu and W. Shi. 2010. "Using DGGE profiling to develop a novel culture medium suitable for oral microbial communities." Mol Oral Microbiol 25(5): 357-367.

Triggs, B., P.F. McLauchlan, R.I. Hartley, and A.W. Fitzgibbon. 2000. "Bundle adjustment—a modern synthesis." In Vision Algorithms: Theory and Practice. Berlin and Heidelberg: Springer, 298-372.

Van Someren, M.W., Barnard, Y.F. and Sandberg, J.A., 1994. "The think aloud method: A practical guide to modelling cognitive processes (vol. 2)." London: Academic Press.

Volgenant, CMC, van der Veen, MH, de Soet, JJ, ten Cate, JM. 2013. "Effect of metallopophyrins on red autofluoescence from oral bacteria," European Journal of Oral Sciences 121:156-161.

Vu, Hoang Hiep. 2011. "Large-scale and high-quality multi-view stereo." PhD dissertation in Informatique, l'Ecole des ParisTech.

Yang, C., Hou, V., Nelson, L.Y., and Seibel, E.J. 2013. "Color-matched and Fluorescence-labeled Esophagus Phantom and its applications," Journal of Biomedical Optics, 18(2): 026020-1-11.

Yang, C., V.W. Hou, E.J. Girard, L.Y. Nelson, and E.J. Seibel. 2014. "Target-to-background enhancement in multispectral endoscopy with real-time background autofluorescence mitigation for quantitative molecular imaging," Journal of Biomedical Optics 19(7):076014.

Young, DA, Novy, BB, Zeller, GG, Hale, R, Hart, TC, Truelove, EL. 2015. "The American Dental Association Caries Classification System for Clinical Practice—A report of the American Dental Association Council on Scientific Affairs," Journal Am Dental Assoc, 146(2): 79-86.

Zhang, L., Nelson, L.Y., and Seibel, E.J. 2011. "Red-shifted fluorescence in sound dental hard tissue," Journal of Biomedical Optics 16(7): 071411-1-5.

Zhang, L., Nelson, L.Y., Berg, J., Seibel, E.J. 2012b. "Spectrally enhanced imaging of occlusal surfaces and artificial shallow enamel erosions with a scanning fiber endoscope," Journal of Biomedical Optics, vol. 17, No. 7, paper # 076019, Jul. 2012.

Zhang, L., Ridge, U.S., Kim, A.S., Nelson, L.Y., Berg, J.H., and Seibel, E.J. 2013. "Tri-modal detection of early childhood caries using laser light scanning and fluorescence spectroscopy—clinical prototype," Journal of Biomedical Optics, 18(11): 111412-1-8.

Albandar, Jasim M. 2002. "Periodontal diseases in North America," Periodontology 2000, 29, 31-69.

American Academy of Pediatric Dentistry (AAPD). 2015. "Guidelines on caries-risk assessment and management for infants, children, and adolescences." Pediatric Dentistry 2015; 37(6): 132-9.

(56) References Cited

OTHER PUBLICATIONS

Blank, M, Friedrich, M., Hamilton, J., Lee, P., Berg, J., and Seibel, EJ. 2011. "Laser scanning dental probe for endodontic root canal treatment," Lasers in Dentistry XVIII, Proc SPIE vol. 7884, 788403-1-7.

Cullinan, MP & Seymour, GJ. 2013. Periodontal disease and systemic illness: will the evidence ever be enough?' Periodontology 2000 62(1):271-286.

Dahlbäck, N., Jönsson, A. and Ahrenberg, L. 1993. "Wizard of Oz studies: why and how." In Proceedings of the 1st International Conference on Intelligent User Interfaces, 193-200. ACM.

Gulino, A, Mineo, P, Scamporrino, E, Vitalini, D, and Fragala, I. 2006. "Spectroscopic and microscopic characterization and behavior of an optical pH meter based on a functional hybrid monolayer molecular system: porphyrin molecules covalently assembled on a molecularly engineered silica surface," Chem Mater 18: 2404-2410.

Küseler, A., V. Baelum, O. Fejerskov and J. Heidmann. 1993. "Accuracy and precision in vitro of Beetrode microelectrodes used for intraoral pH measurements." Caries Res 27(3): 183-190.

Leonard, JJ, Yonetani, T, and Callis, JB 1974. "A fluorescence study of hybrid hemoglobins containing free base and zinc protoporphyrin IX," Biochemistry, 13(7): 1460-1464.

Ng, MW and Chase, I. 2013. "Early Childhood Caries, risk-based disease prevention and management," Dental Clinics of N Am, 57:1-16.

Rugg, A.L. Nelson, L.Y., Timoshchuk, M.- A., and Seibel, E.J. 2015. "Design and fabrication of a disposable dental handpiece for clinical use of a new laser-based therapy monitoring system," ASME J. Med Devices, 10(1):011005-011005-10, MED-15-1178, Dec. 4, 2015.

Samnaliev, M, Wijeratne, R, Kwon, EG, Ohiomoba, H, and Ng, MW. 2015. "Cost-effectiveness of a disease management program for early childhood caries," J Public Health Dentistry 75:24-33.

Seibel, EJ, Soper, TD, Burkhardt, MR, Porter, MP, and Yoon, WJ. 2012. "Multimodal flexible cystoscopy for creating co-registered panoramas of the bladder urothelium," Therapeutics and Diagnostics in Urology, Proc. SPIE vol. 8207B,82071A-1-7.

Soper, T.D., M.P. Porter, and E.J. Seibel. 2012. "Surface mosaics of the bladder reconstructed from endoscopic video for automated surveillance." IEEE Transactions on Biomedical Engineering 59(6):1670-1680.

Thompson, F. C. and F. Brudevold. 1954. "A micro-antimony electrode designed for intraoral pH measurements in man and small experimental animals." J Dent Res 33(6): 849-853.

Timoshchuk, M.-A.I., Ridge, J.S, Rugg, A.L., Nelson, L.Y., Kim, A.S, and Seibel, E.J. 2015. "Real-time porphyrin detection in plaque and caries—a case study," Lasers in Dentistry XXI, Proc. SPIE vol. 9306, paper # 93060C-1-11.

Timoshchuk, M.-A., Zhang, L., Dickinson, B.A., Ridge, J.S., Kim, A.S., Baltuck, C.T., Nelson, L.Y., Berg, J.H., and Seibel, E.J. 2014. "Guided fluorescence diagnosis of childhood caries: preliminary measures correlate with depth of carious decay," Lasers in Dentistry XX, Proc. SPIE vol. 8929, paper 892904-1-9.

Vega, K., Kennedy, M., Nelson, L., Seibel, E.J., Shin, D., Meredith, C., Pruel, M., and Bichard, W. (In press). "Cell-size Microsphere Phantom for Determining Surgical Detection Sensitivity to Porphyrin," SPIE Translational Biophotonics 2016, Houston, TX, May 2016.

Zhang, L, Nelson, LY, Berg, JH, Eichenholz, J, and Seibel, EJ. 2012a. "Optical measure of enamel health, ability to triage high risk children in communities without dental practitioners," IEEE Global Humanitarian Technology Conference, DOI 10.1109/GHTC.2012. 52, pp. 345-349.

D. Spitzer et al., "The Absorption and Scattering of Light in Bovine and Human Dental Enamel," Calcified Tissue Research, 17(2):129-137 (1975).

JBD Featherstone et al., "A Mechanism for Dental Caries Based on Chemical Processes and Diffusion Phenomena During In-Vitro Caries Simulation on Human Tooth Enamel," Archives of Oral Biology, 24(2):101-112 (1979).

SA Prahl et al., "A Monte Carlo Model of Light Propagation in Tissue," SPIE Proceedings of Dosimetry of Laser Radiation in Medicine and Biology, IS 5:102-111 (1989).

L. Giniunas et al., "Endoscope With Optical Sectioning Capability," Applied Optics, 32(16):2888-2890 (1993).

D. Fried et al., "Nature of Light Scattering in Dental Enamel and Dentin at Visible and Near-Infrared Wavelengths," Applied Optics, 34(7):1278-1285 (1995).

LH Wang et al., "MCML—Monte Carlo Modeling of Photon Transport in Multi-Layered Tissues," Computer Methods and Programs in Biomedicine, 47(2):131-146 (1995).

JR Zijp et al., "HeNe-Laser Light Scattering By Human Dental Enamel," Journal of Dental Research, 74(12):1891-1898 (1995).

OM Winn et al., "Coronal and Root Caries in the Dentition of Adults in the United States, 1988-1991," Journal of Dental Research, 75:642-651 (1996).

KJ Anusavice., "Management of Dental Caries as a Chronic Infectious Disease," Journal of Dental Education, 62(10):791-802 (1998).

BW Colston Jr et al., "Dental OCT," Optics Express, 3(6):230-238 (1998).

BW Colston Jr et al., "Imaging of Hard- and Soft-Tissue Structure in the Oral Cavity By Optical Coherence Tomography," Applied Optics, 37(16):3582-3585 (1998).

KR Ekstrand et al., "Detection, Diagnosing, Monitoring and Logical Treatment of Occlusal Caries in Relation to Lesion Activity and Severity. An In Vivo Examination With Histological Validation," Caries Research, 32(4):247-254 (1998).

F. Feldchtein et al., "In Vivo OCT Imaging of Hard and Soft Tissue of the Oral Cavity," Optics Express, 3(6):239-250 (1998).

Ferreira Zandona et al., "Laser Fluorescence Detection of Demineralization in Artificial Occlusal Fissures," Caries Research, 32(1):31-40 (1998).

AG Almeida et al., "Future Caries Susceptibility in Children With Early Childhood Caries Following Treatment Under General Anesthesia," Pediatric Dentistry, 22(4):302-306 (2000).

FLL Otis et al., "Optical Coherence Tomography: A New Imaging Technology for Dentistry," Journal of the American Dental Association, 131(4):511-514 (2000).

C. Robinson et al., "The Chemistry of Enamel Caries," Critical Reviews in Oral Biology and Medicine, 11(4):481-495 (2000).

J. Bush et al., "All-Fiber Optic Coherence Domain Interferometric Techniques," Fiber Optic Sensor Technology II, 4204:71-80 (2001).

J. Knittel et al., "Endoscope-Compatible Confocal Microscope Using a Gradient Index-Lens System," Optics Communications, 188(5-6):267-273 (2001).

P. Niederer et al., "Image Quality of Endoscopes," Biomonitoring and Endoscopy Technologies, Proceedings of SPIE, 4158:1-10 (2001).

EJ Seibel et al., "Single Fiber Flexible Endoscope: General Design for Small Size, High Resolution, and Wide Field of View," Biomonitoring and Endoscopy Technologies, Proceedings of SPIE, 4158:29-39 (2001).

QYJ Smithwick et al., "Control Aspects of the Single Fiber Scanning Endoscope," Optical Fibers and Sensors for Medical Applications, Proceedings of SPIE, 4253:176-188 (2001).

ME Fauver et al., "Microfabrication of Fiber Optic Scanners," Optical Scanning 2002, Proceedings of SPIE, 4773:102-110 (2002).

D Fried et al., "Imaging Caries Lesions and Lesion Progression With Polarization Sensitive Optical Coherence Tomography," Journal of Biomedical Optics, 7(4):618-627 (2002).

D. Fried et al., "Imaging Caries Lesions and Lesion Progression With Polarization-Sensitive Optical Coherence Tomography," Lasers in Dentistry VIII, 4610:113-124 (2002).

RS Jones et al., "Attenuation of 1310- and 1550-nm Laser Light Through Sound Dental Enamel," Lasers in Dentistry VIII, 4610:187-190 (2002).

EJ Seibel et al., "Prototype Scanning Fiber Endoscope," Optical Fibers and Sensors for Medical Applications II, Proceedings of the SPIE, 4616:173-179 (2002).

EJ Seibel et al., "Unique Features of Optical Scanning, Single Fiber Endoscopy," Lasers in Surgery and Medicine, 30(3):177-183 (2002).

(56) References Cited

OTHER PUBLICATIONS

QYJ Smithwick et al., "Depth Enhancement Using A Scanning Fiber Optical Endoscope," Optical Biopsy IV, Proceedings of SPIE, 4613:222-233 (2002).
N Tinanoff et al., "Clinical Decision Making for Caries Management in Children," Pediatric Dentistry, 24(5):386-392 (2002).
AI Ismail, "Determinants of Health in Children and the Problem of Early Childhood Caries," Pediatric Dentistry, 25(4):328-333 (2003).
National Institute of Dental and Craniofacial Research., "Dental Caries (Tooth Decay) in Children (Age 2 to 11)," NIDCR (2011).
Zhang et al., "Spectrally Enhanced Image Resolution of Tooth Enamel Surfaces," Lasers in Dentistry XVIII, Proceedings of SPIE, 8208:82080F-1-15 (2012).
C Yang et al., "Mitigating Fluorescence Spectral Overlap In Wide-Field Endoscopic Imaging," Journal of Biomedical Optics, 18(8):086012-1-13 (2013).
Wikipedia, "Methylene blue," available online at: http://en.wikipedia.org/wiki/Methylene_blue (2016).
CM Brown et al., "Mechanical Design and Analysis for a Scanning Fiber Endoscope," Proceedings of the 2001 ASME International Mechanical Engineering Congress and Exposition, 51:165-166 (2001).
Gong et al., "Three-dimensional measurement of small inner surface profiles using feature-based 3-D panoramic registration," Optical Engineering, vol. 56, No. 1, Jan. 2017, 10 pages.
Wencel, D., et al., "Optical Chemical pH Sensors," Analytical Chemistry, 2014, vol. 86, pp. 15-29.
Wróbel, D., et al., "Charged Porphyrin—dopa Melanin Interaction at Varied pH: Fluorescence Lifetime and Photothermal Studies," Journal of Fluorescence, 2003, vol. 13, No. 2, pp. 169-177.
Yoshitani, T., et al., "LumiO: A Plaque-aware Toothbrush," UbiComp. 2016 Proceedings of the 2016 ACM International Joint Conference on Pervasive and Ubiquitous Computing, pp. 605-615.
Yuvaraj, M., et al., "Fluorescence spectroscopic characterization of salivary metabolites of oral cancer patients," Journal of Photochemistry and Photobiology B: Biology, 2014, vol. 130, pp. 153-160.
Hope, C.K., et al., "Reducing the variability between constant-depth film fermenter experiments when modelling oral biofilm," Journal of Applied Microbiology, 2012, vol. 113, No. 3, pp. 601-608.
Liu, Q., et al., "A novel rapid method for simultaneous determination of three diagnostically important porphyrins in erythrocytes using hyphenated synchronous fluorescence techniques," Talanta, 2012, vol. 88, pp. 663-668.
Agarwal, N., et al., "DNA Ploidy Measure of Feulgen-Stained Cancer Cells using Three-Dimensional Image Cytometry," IEEE EMBS Special Topic Conference on Healthcare Innovation & Point-of-Care Technologies, Seattle, WA, Oct. 8-10, 2014, pp. 6-9.
Asai, A., "Studies on relationship between bacterial flora and shift in pH of periodontal pockets in adult periodontitis," Aichi-Gakuin J. Dent. Sci., 1993, vol. 31, No. 1, pp. 1-21.
Biswas, S., et al., "Use of MALDI-TOF mass spectrometry for identification of bacteria that are difficult to culture," Journal of Microbiological Methods, 2013, vol. 92, No. 1, pp. 14-24.
Bittar, D.G., et al., "Is the red fluorescence of dental plaque related to its cariogenicity?" Journal of Biomedical Optics, 2014, vol. 19, No. 6, 7 pages.
Brazier, J.S., et al., "A note on ultra-violet red fluorescence of anaerobic bacteria in vitro," Journal of Applied Bacteriology, 1986, vol. 60, No. 2, 7 pages.
Brown, S.B., et al., "Equilibrium and Kinetic Studies of the Aggregation of Porphyrins in Aqueous Solution," Biochem. J., 1976, vol. 153, No. 2, pp. 279-285.
Buchalla, W., et al., "Fluorescence spectroscopy of dental calculus," Journal of Periodontal Research, 2004, vol. 39, No. 5, pp. 327-332.
Byrne, D.P., et al., "Evidence of mutualism between two periodontal pathogens: co-operative haem acquisition by the HmuY haemophore of Porphyromonas gingivalis and the cysteine protease interpain A (InpA) of Prevotella intermedia," Molecular Oral Microbiology, 2013, vol. 28, No. 3, pp. 219-229.

Coe, R.L., et al., "Computational modeling of optical projection tomographic microscopy using the finite difference time domain method," Journal Optical Society of America A, 2012, vol. 29, No. 12, pp. 2696-2707.
Coe, R.L., et al., "Experimental and theoretical analysis for improved microscope design of optical projection tomographic microscopy," Optics Letters, 2013, vol. 38, No. 17, pp. 3398-3401.
Coe, R.L., et al., "Improved near-field calculations using vectorial diffraction integrals in the finite-difference time-domain method," Journal Optical Society of America A, 2011, vol. 28, No. 8, pp. 1776-1783.
Coe, R.L., et al., "Isometric 3D Imaging of Cellular Samples Using Optical Projection Tomographic Microscopy," Advanced Biophotonics: Tissue Optical Sectioning, 2013, pp. 581-620.
Coulthwaite, L., et al., "The Microbiological Origin of Fluorescence Observed in Plaque on Dentures during QLF Analysis," Caries Research, 2006, vol. 40, No. 2, pp. 112-116.
De Bruijn, H.S., et al., "Light fractionated ALA-PDT enhances therapeutic efficacy in vitro; the influence of PpIX concentration and illumination parameters," Photochemical & Photobiological Sciences, 2013, vol. 12, No. 12, pp. 241-245.
De Josselin de Jong, E., et al., "A New Method for in vivo Quantification of Changes in Initial Enamel Caries with Laser Fluorescence," Caries Research, 1995, vol. 29, No. 1, 8 pages.
Dietel, W., et al., "5-Aminolaevulinic acid (ALA) induced formation of different fluorescent porphyrins: A study of the biosynthesis of porphyrins by bacteria of the human digestive tract," Journal of Photochemistry and Photobiology B: Biology, 2007, vol. 86, No. 1, pp. 77-86.
Dong, Y.M., et al., "Plaque pH and Associated Parameters in Relation to Caries," Caries Research, 1999, vol. 33, pp. 428-436.
Fiyaz, M., et al., "Association of salivary calcium, phosphate, pH and flow rate on oral health: A study on 90 subjects," Journal of Indian Society of Periodontology, 2013, vol. 17, No. 4, 5 pages.
Fontana, M., et al., "Assessing patients' caries risk," JADA, 2006, vol. 137, No. 9, pp. 1231-1239.
Gulino, A., et al., "Optical PH Meter by Means of a Porphyrin Monolayer Covalently Assembled on a Molecularly Engineered Silica Surface," Chem. Mater., 2005, vol. 17, pp. 4043-4045.
Haffajee, A.D., et al., "Microbial complexes in supragingival plaque," Oral Microbiology Immunology, 2008, vol. 23, No. 3, pp. 196-205.
Hope, C.K., et al., "Evaluating the effect of local pH on fluorescence emissions from oral bacteria of the genus *Prevotella*," Journal of Biomedical Optics, 2016, vol. 21, No. 8, 5 pages.
Igarashi, S., et al., "Optical pH Sensor of Electrostatically Immobilized Porphyrin on the Surface of Sulfonated-Polystyrene," Analytical Sciences, 1994, vol. 10, No. 5, pp. 821-822.
Kim, Y.S., et al., "Monitoring the maturation process of a dental microcosm biofilm using the Quantitative Light-induced Fluorescence-Digital (QLF-D)," Journal of Dentistry, 2014, vol. 42, No. 6, pp. 691-696.
Koenig, K., et al., "Laser-induced autofluorescence of carious regions of human teeth and caries-involved bacteria," SPIE Proceedings, 1993, vol. 2080, Dental Applications of Lasers, 12 pages.
Lee, E.S, et. al., "Association between the cariogenicity of a dental microcosm biofilm and its red fluorescence detected by Quantitative Light-induced Fluorescence-Digital (QLF-D)," Journal of Dentistry, 2013, vol. 41, No. 12, pp. 1264-1270.
Lin, D.L., et al., "Rapid and Simultaneous Determination of Coproporphyrin and Protoporphyrin in Feces by Derivative Matrix Isopotential Synchronous Fluorescence Spectrometry," Clinical Chemistry, 2004, vol. 50, No. 10, pp. 1797-1803.
Liu, Y.Y., et al., "Colorimetric and Fluorescent Bimodal Ratiometric Probes for pH Sensing of Living Cells," Chemistry: An Asian Journal, 2015, vol. 10, pp. 1304-1310.
Marsh, P.D., "Are dental diseases examples of ecological catastrophes?" Microbiology, 2003, vol. 149, pp. 279-294.
Martinez-Olmos, A., et al., "Sensor array-based optical portable instrument for determination of pH," Sensors and Actuators B, 2011, vol. 156, pp. 840-848.
Matošević, D., et al., "The Detection of Carious Lesion Porphyrins Using Violet Laser Induced Fluorescence," Acta Stomatologica Croatica, 2010, vol. 44, No. 4, pp. 232-240.

(56) References Cited

OTHER PUBLICATIONS

Melø, T.B., et al., "The Physicochemical State of Protoporphyrin IX in Aqueous Solution Investigated by Fluorescence and Light Scattering," Biophysical Chemistry, 1986, vol. 25, pp. 99-104.

Miao, Q., et al., "Multimodal 3D Imaging of Cells and Tissue, Bridging the Gap Between Clinical and Research Microscopy," Annals of Biomedical Engineering, 2012, vol. 40, No. 2, pp. 263-276.

Miao, Q., et al., "Resolution improvement in optical projection tomography by the focal scanning method," Optics Letters, 2010, vol. 35, No. 20, pp. 3363-3365.

Mills, C., et al., "Adopting caries risk assessment in all practice environments," General Dentistry, 2016, vol. 64, No. 4, 8 pages.

Montcel, B., et al., "Two-peaked 5-ALA-induced PpIX fluorescence emission spectrum distinguishes glioblastomas from low grade gliomas and infiltrative component of glioblastomas," Biomedical Optics Express, 2013, vol. 4, No. 4, pp. 548-558.

Nakata, K., et al., "Relationship between fluorescence loss of QLF and depth of demineralization in an enamel erosion model," Dental Materials Journal, 2009, vol. 28, No. 5, pp. 523-529.

Niu, C.G., et al., "A ratiometric fluorescence sensor with broad dynamic range based on two pH-sensitive fluorophores," The Analyst, 2005, vol. 130, pp. 1551-1556.

Pretty, I.A., et al., "Quantification of dental plaque in the research environment," Journal of Dentistry, 2005, vol. 33, pp. 193-207.

Rajesh, K., et al., "Assessment of salivary calcium, phosphate, magnesium, pH, and flow rate in healthy subjects, periodontitis, and dental caries," Contemporary Clinical Dentistry, 2015, vol. 6, No. 4, pp. 461-465.

Rice, Z., et al., "Adsorption characteristics of a cationic porphyrin on nanoclay at various pH," Journal of Colloid and Interface Science, 2009, vol. 335, No. 2, pp. 189-195.

Scolaro, L.M., et al., "Aggregation Behavior of Protoporphyrin IX in Aqueous Solutions: Clear Evidence of Vesicle Formation," J. Phys. Chem. B, 2002, vol. 106, No. 10, pp. 2453-2459.

Slots, J., et al., "Long-Wave UV Light Fluorescence for Identification of *Black-Pigmented Bacteroides* spp.," Journal of Clinical Microbiology, 1982, vol. 16, No. 6, pp. 1148-1151.

Smalley, J.W., et al., "The haem pigment of the oral anaerobes Prevotella nigrescens and Prevotella intermedia is composed of iron(III) protoporphyrin IX in the monomeric form," Microbiology, 2003, vol. 149, No. 7, pp. 1711-1718.

Soukos, N.S., et al., "Phototargeting Oral Black-Pigmented Bacteria," Antimicrobial Agents and Chemotherapy, 2005, vol. 49, No. 4, pp. 1391-1396.

Stephan, R.M., "Intra-Oral Hydrogen-Ion Concentrations Associated with Dental Caries Activity," J. Dent. Res., 1944, vol. 23, pp. 257-266.

Valentine, R.M., et al., "Modelling fluorescence in clinical photodynamic therapy," Photochemical & Photobiological Sciences, 2013, vol. 12, pp. 203-213.

Van der Veen, M.H., et al., "Red Autofluorescence of Dental Plaque Bacteria," Caries Research, 2006, vol. 40, No. 6, pp. 542-545.

Vaughan, A.A., et al., "Optical Ammonia Sensing Films Based on an Immobilized Metalloporphyrin," Analytical Communications, 1996, vol. 33, No. 11, pp. 393-396.

Vetrova, E.V., et al., "Characteristics of endogenous flavin fluorescence of Photobacterium leiognathi luciferase and Vibrio fischeri NAD(P)H:FMN-oxidoreductase," Luminescence, 2005, vol. 20, No. 3, pp. 205-209.

\* cited by examiner

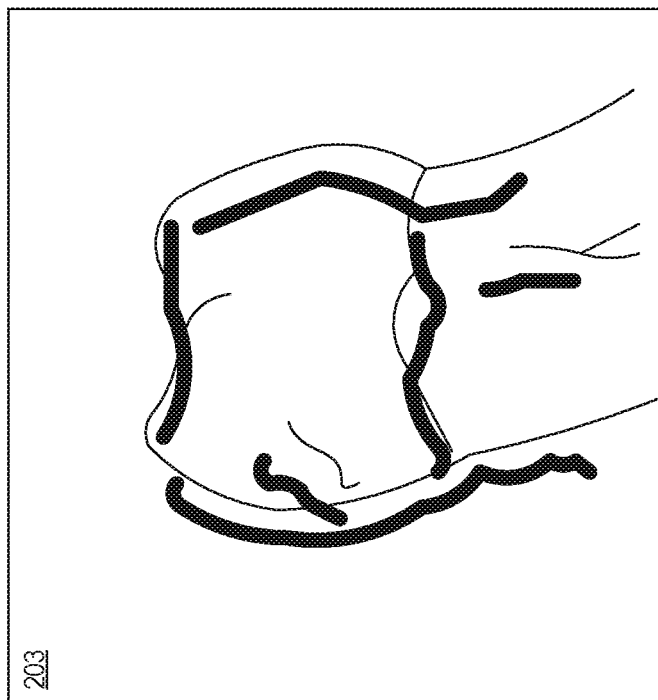
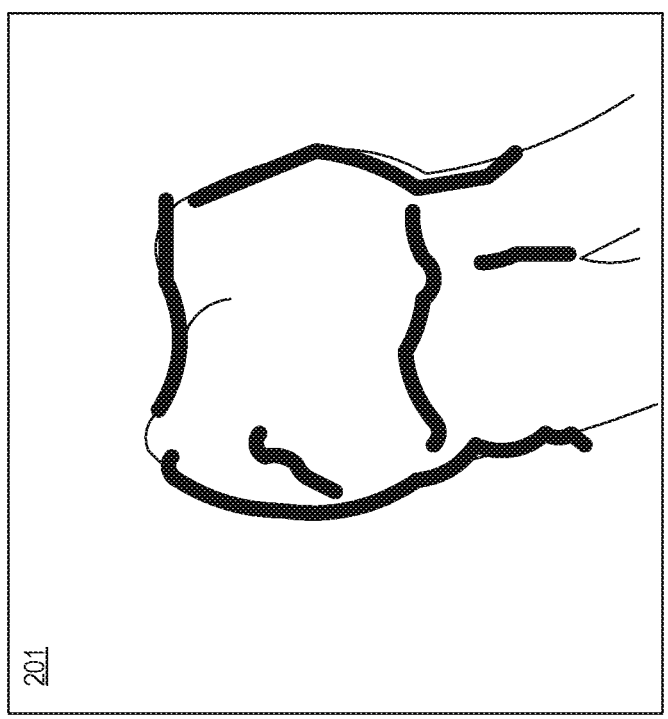
FIG. 2

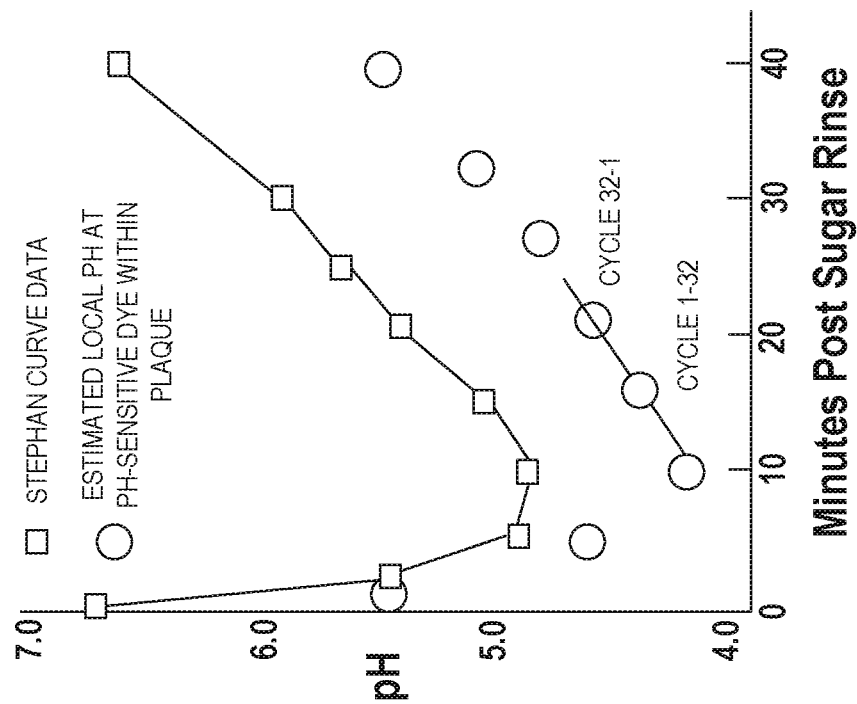
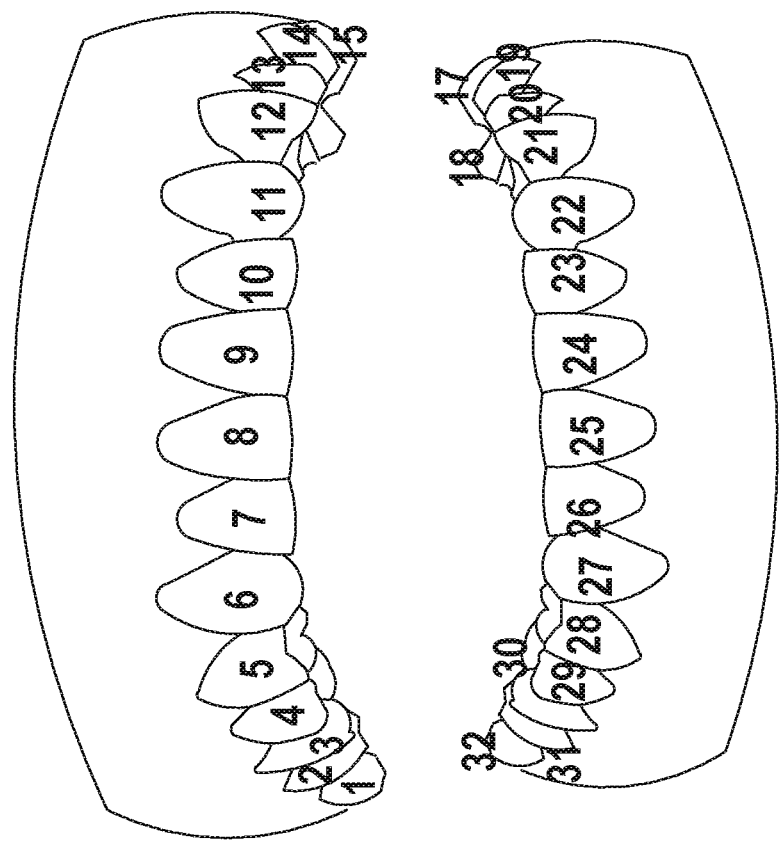
FIG. 4

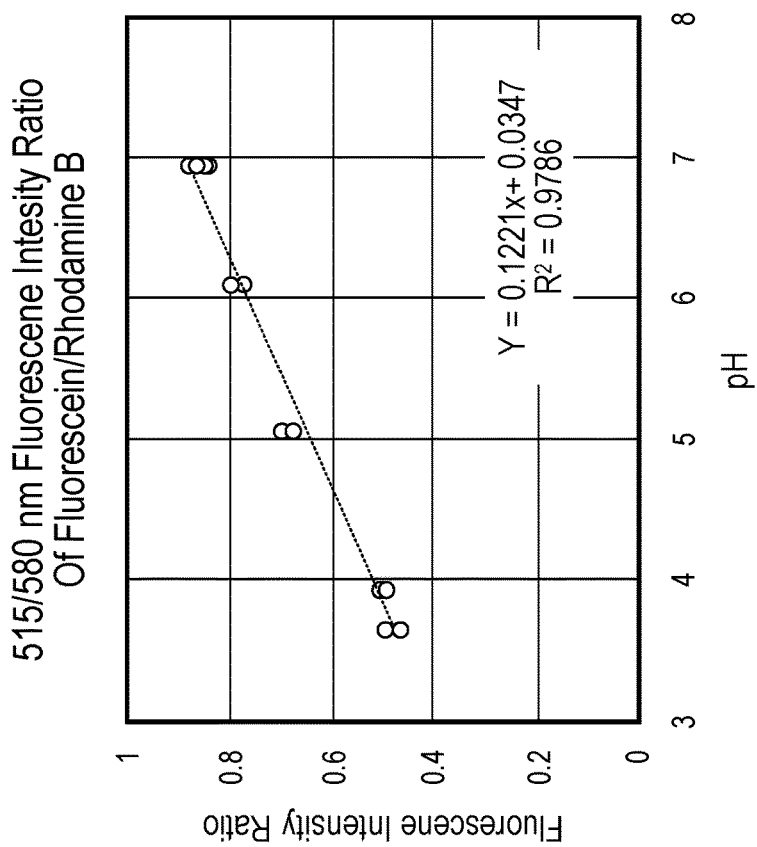
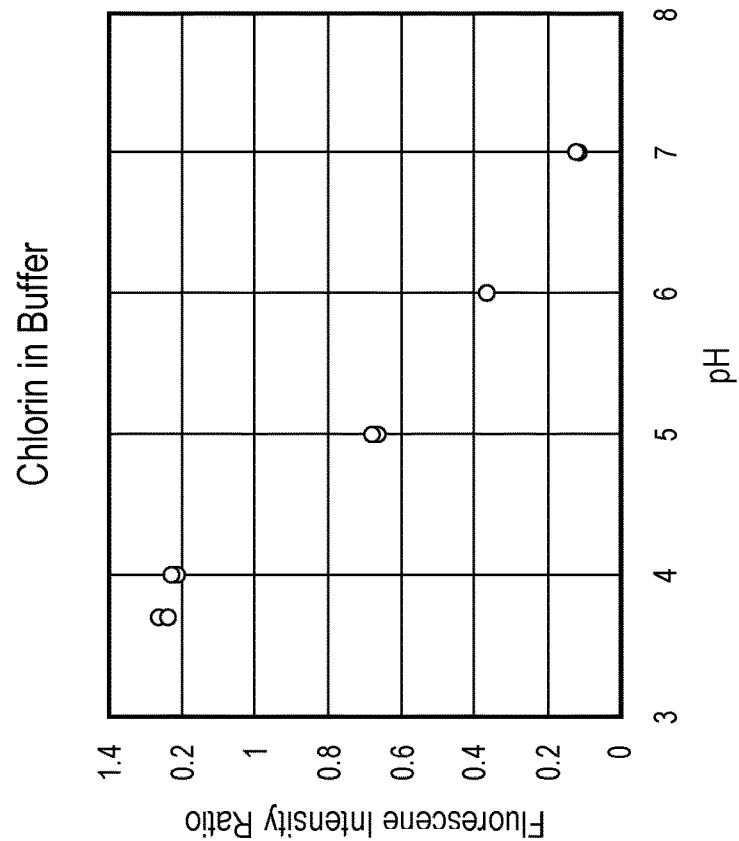
FIG. 11A

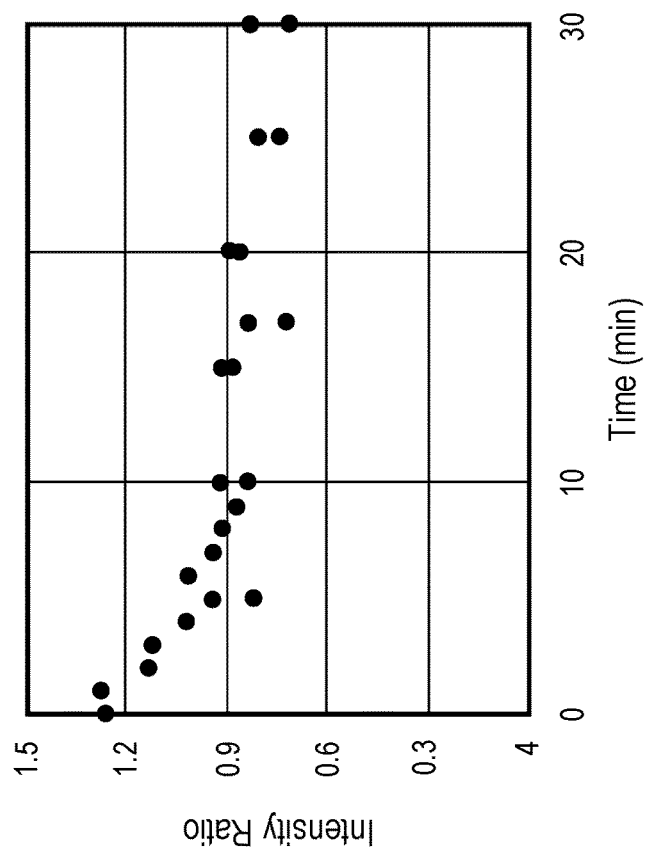
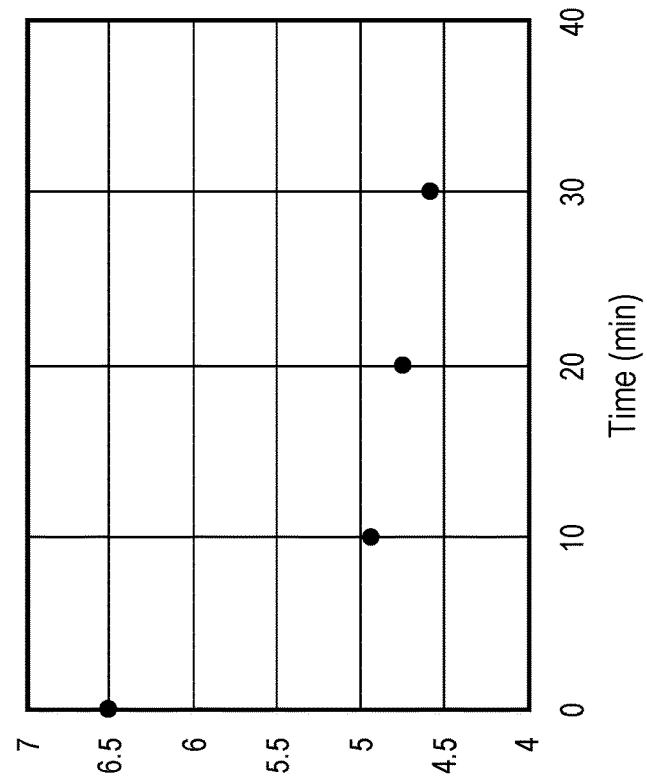
FIG. 11B

SYSTEM AND METHOD FOR RANKING BACTERIAL ACTIVITY LEADING TO TOOTH AND GUM DISEASE

CROSS-REFERENCE TO RELATED APPLICATIONS

This application claims priority to U.S. Provisional Patent Application No. 62/414,581, filed on Oct. 28, 2016. U.S. Provisional Patent Application No. 62/414,581 is hereby incorporated by reference.

GOVERNMENT LICENSE RIGHTS

This invention was made with government support under Grant No. 1631146, awarded by the National Science Foundation (NSF). The government has certain rights in the invention.

TECHNICAL FIELD

This disclosure relates generally to dental hygiene, and in particular but not exclusively, relates to detection of bacterial activity.

BACKGROUND INFORMATION

In 2010, untreated caries in permanent teeth was the most prevalent disease condition worldwide, affecting 2.4 billion people. Although preventable, caries is the most common chronic disease in children and adolescents between the ages of 6 and 19 years; early childhood caries (ECC) leads to pain, infection, and discomfort, negatively affecting quality of life and causing significant economic and social burden on children, families, and society. ECC rates are rising in the USA. Minority and low-income families are disproportionally affected and less likely to receive timely care, the lack of which escalates the cost. Hospital emergency departments and operating rooms are frequently utilized for the treatment of ECC, a costly and inefficient use of hospital resources.

It has been recognized that surgical and restorative treatment does not cure or address dental caries as a disease. Prevention plans, remineralization activities, and at-home protocols and programs to promote oral health and halt or reverse caries progression have been associated with decreased surgical and restorative visits and hospital utilization, thus lowering the overall cost of disease management. Our society has demonstrated the acceptance of low-cost health monitors in medicine and healthcare providers use and continue to adopt the high-efficiency of telehealth procedures, especially in rural areas. Treatment options for dental caries include remineralization agents with subsequent professional and home monitoring of the disease progression. These treatments require the combination of self-care at home and in-office care with a dentist. However, currently there are hardly any dental imaging and diagnostic instruments that can be used outside the clinic.

BRIEF DESCRIPTION OF THE DRAWINGS

Non-limiting and non-exhaustive examples of the invention are described with reference to the following figures, wherein like reference numerals refer to like parts throughout the various views unless otherwise specified.

FIG. 2 shows an embodiment of feature based relocation, in accordance with the teachings of the present disclosure.

FIG. 4 depicts an embodiment of numbering and measuring of suspicious regions in a mouth, in accordance with the teachings of the present disclosure.

FIGS. 11A-11B illustrate successful experimental results of the techniques described herein, in accordance with the teachings of the present disclosure.

Figure 1A:
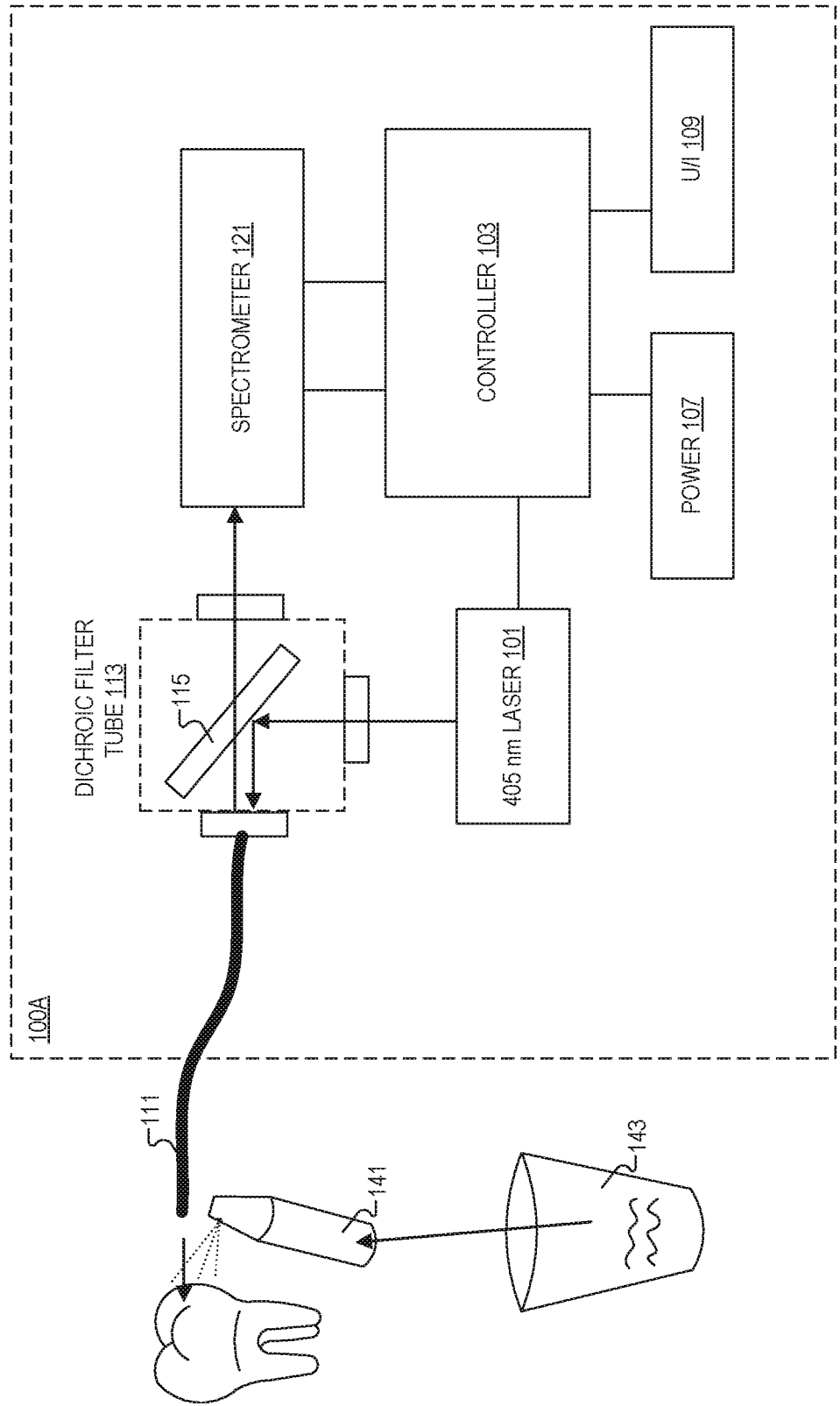
FIG. 1A illustrates one embodiment of a device to anticipate demineralization, in accordance with the teachings of the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

Examples of an apparatus and method relating to ranking bacterial activity leading to tooth and gum disease are described herein. In the following description, numerous specific details are set forth to provide a thorough understanding of the examples. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one example" or "one embodiment" means that a particular feature, structure, or characteristic described in connection with the example is included in at least one example of the present invention. Thus, the appearances of the phrases "in one example" or "in one embodiment" in various places throughout this specification are not necessarily all referring to the same example or embodiment. Furthermore, the particular features, structures, or characteristics may be combined in any suitable manner in one or more examples or embodiments.

Cariogenic bacteria in the oral cavity generate acid during metabolism of nutrients like sugar. Once the pH value is under 5.5, it will result in demineralization of enamel. The saliva flow that contains buffering and is supersaturated with calcium ions as well as bacterial metabolism of urea and arginine into ammonia is key to raise pH back to resting pH levels, and helps remineralize teeth. The fast pH drop after meal/sugar challenge and the recovery back to resting pH directly shows the acidic environment resulting from sugar ingestion, bacteria activity, saliva flow, etc. This determines the demineralization and remineralization balance of teeth. The resting pH and the dynamic pH response (i.e., different rates of acid increase or decrease) after sugar challenge are indicators for cariogenic bacteria activity and thus may serve as robust precursors for prediction. The changing pH profile after a carbohydrate (sugar) rinse contains information that can distinguish cariogenic status (e.g., the drop and duration of low pH are greater in carious regions). Lowest pH values are similar in both a high caries patient and a caries-free patient. But pH recovery rates show variance between high caries and caries-free subjects. This confirms that pH recovery rate is also an important factor to distinguish different carious regions. It is worth noting that measurements using electrical pH meter may have limited capability to measure pH locally and non-invasively.

Optical pH sensing may be accomplished with two methods: absorption-based/colorimetric pH sensing, and fluorescence-based pH sensing. Absorption-based sensing can be implemented by measuring the light transmission through extracted saliva with additional dye, or the reflected light may be measured from tooth surfaces in-vivo/in-vitro. Because measurements are taken in-vitro on saliva, the decrease is much slower and also there is no pH recovery from saliva flow. Additionally, bulky transmission mode testing equipment is hard to use in vivo.

Fluorescence-based pH sensing for oral caries makes use of pH-induced spectral change of Protoporphyrin IX (PpIX) to take reliable, non-invasive measurements of pH. Derivatives of PpIX, which have enhanced pH sensitivity, or other dyes can also be added. In addition to porphyrin and fluorescein, other molecules that are indicative of the metabolic activity, amount, composition, or progression of oral biofilms that are associated with tooth decay and gum disease can also be monitored optically, with or without addition of chemicals, foods, or molecules. Accumulation of porphyrin compounds (protoporphyrin IX, zinc protoporhyrin, coproporphyrin etc.) on dental enamel surfaces and near the gum lines are by-products of bacterial metabolism and can serve as early indicators of dental disease. Therefore, a dental imaging camera that can detect the early appearance of porphyrin compounds is a valuable complement to visual inspection of dental health by a clinician.

Quantitative measurement of fluorescence-based pH sensing may be limited by PpIX thermal/photochemical stability, unstable illumination from variance in equipment performance, and variance of fluorophore concentration. To conquer these possible limitations, various detection methodology will be applied and explored herein. There are two main detection techniques that can eliminate the influence of environmental factors, such as light variance and temperature fluctuation. One is intensity ratiometric method; the other is lifetime-based sensing.

The intensity ratiometric method takes the ratio of fluorescence or reflectance intensity of two different emission wavelengths: one reference wavelength which has invariant emission intensity under changing pH, the other wavelength which is highly-sensitive to pH variance (it can also be a combination of two wavelengths which are both sensitive to pH variance but whose difference in sensitivity changes with variant pH). By taking the ratio of two wavelengths, the user can nullify the inference from illumination variance, fluorophore concentration, and small photo-bleaching effect (assuming the photobleaching effect isn't fast enough to kill all fluorophores before the measurement is taken). Intensity ratiometric method may be done by finding an isosbestic point, which is a certain wavelength where the absorption or fluorescent emission intensity doesn't change with pH. The isosbestic point serves as a reference wavelength. By taking the ratio of intensities at the pH-sensitive wavelength with the reference wavelength, the environmental interference is nullified. However, the pH-induced spectral change of PpIX may not display an isosbestic point due to the shift of its peak wavelength. Under acidic conditions (pH<6) the PpIX fluorescence exhibits a peak at 634 nm that steadily increases in intensity as the pH is reduced (more acidic). Under basic conditions (pH>8) the fluorescence shifts to a new feature with a peak at 620 nm that steadily increases with increasing pH. Looking into the relative intensity change of the four characteristic peak wavelengths, the changing difference between 620 nm and 634 nm peak can correlate well with pH value in the range of 4 to 7.

Lifetime-based sensing correlates the change in fluorescence or phosphorescence lifetime with pH. There are two methods for lifetime measurement: the time-domain method (which detects time-resolved emission profile $I(t)=I_0 \exp(-t/\tau)$, and then extract lifetime information by measuring the time when emission intensity is $1/e$ of the maximum value), and the frequency-domain method (which uses modulated excitation light, and then measures the phase difference or amplitude modulation of the emission intensity). Lifetime information can be extracted from either phase information or modulation information using equations $\tan \varphi = \omega \tau_\varphi$ where the phase angle $\varphi$ is the phase delay measured from the zero-crossing times of the modulated components, $$m = \frac{1}{\sqrt{1+\omega^2 \tau_m^2}},$$

where $m=(B/A)/(b/a)$ is the demodulation factor and is often called the modulation, B and b are respectively half of peak to peak value in emission and excitation signal, A and a are respectively offset value in emission and excitation signal. Extraction of lifetime information from time-domain or frequency-domain information may both require robust curve fitting method such as the most widely used nonlinear least-square fitting, and also global analysis and maximum entropy method, which are suitable for emission profile with multiple lifetimes.

Lifetime measurements eliminate environment interference (such as illumination variance, fluorophore concentration) intrinsically, since absolute intensity values don't influence lifetime. Moreover, lifetime measurements eliminate the influence of photobleaching (which takes seconds) while lifetime measurements are on the order of $10^{-9}$ s in fluorescence, and $10^{-3}$ s in phosphorescence. However, there may be limitations in lifetime-based sensing. Lifetime based measurement may require more expensive instruments. Moreover, lifetime measurements may be influenced by collisional quenching (caused by collision of an excited state fluorophore and another molecule in solution). This problem is easier to solve through eliminating molecules in the oral environment that may influence lifetime.

The instant disclosure includes embodiments directed at an easy-to-use and robust solution for the prediction of caries development, and monitoring of caries progression based on intra-oral fluorescence-based pH sensing. This technique is able to provide self-monitoring for home use (as well as for remote supervision applications), and severity ranking for clinical risk assessment.

In one embodiment, a device may include optical spectroscopic measuring for reflectance, fluorescence, and/or phosphorescence measurements that indicate a pH value or pH change induced by a sugar challenge. The sugar challenge may include rinsing the mouth (teeth and gums) with a sucrose solution that may contain chemicals that enhance the optical pH signal from plaque and bacteria, such as zinc compounds and/or fluorescein dyes. It is appreciated this could be performed with a laser and spectrophotometer. The process could also be performed with light emitting diodes (LEDs) and three optical filters with three spectral bands (like red, green, and blue) that filter optical data to a camera sensor. The optical spectroscopic measuring may further include a spray nozzle that can create a local sugar environment for the measurement of pH (absolute or relative) during a period of time. The device may also include integration of a camera or a scanning light imager that creates a times series of images with reflectance, fluorescence, and/or phosphorescence contrast. Integration of 3D image stitching and reconstruction algorithms for the spatial localization and display of the bacterial loading on the teeth, gums and other soft tissues may also be included. Likewise, optical measurement can use the fluorescence or phosphorescence intensity or lifetime measurements, which are correlated with pH changes of the specific molecule of interest. Optical measures are not limited to the visible spectrum. Polarization filtering may be used to reduce specular reflections which create artifacts in the optical measurements listed above.

Embodiments of a method for measuring dental decay may include measuring/mapping resting pH or the fluorescence signal of all possible tooth surfaces to identify regions with caries/disease risk. Regions with relatively low resting pH and strong PpIX fluorescence may be considered to be the regions of interest (ROI). Resting pH of ROIs may also be the baseline for further measurement and may be one of the factors that determine risk assessment. In one embodiment, after a sugar challenge to the entire oral cavity, one may measure the pH value(s) of all regions of interest (e.g., regions where there are plaque deposits with sufficient signal), and then at another time, measure again to obtain the average pH value relative to all other regions of interest. For example, a user may measure fluorescent plaque deposits in numerical teeth order, and then repeat this measurement in reverse numerical order, taking the average of the two measurements for each region of interest ROI. In this way, one can obtain the pH value at the same average time points for all ROIs. In one embodiment, after applying a local sugar challenge to the region of interest, measuring the value(s) of pH at or within a certain time period, and extracting information about resting pH, and pH recovery rate, the system may provide caries risk assessment. In addition to the sugar challenge, spinach extract could also be added to quickly promote PpIX formation in a variety of dental bacteria.

Alternate or additional embodiments may further include integration of personal hygiene devices, such as a water delivery device to deliver sugar free solution. The sugar free solution can also contain dye molecules that are an optical pH indicator (e.g., fluorescein), and/or chemicals (e.g., zinc) that enhance the optical signal from pH changes to the natural porphyrin dye. These techniques and devices may be used to measure bacterial activity in other soft tissue regions of the mouth and throat for management of other ailments such as cold sores, infections, and bad breath. In addition, these techniques can be used for other regions of the body and for open and closed wounds.

Further it is appreciated that early detection of caries is a critical component of preventative dentistry and that patient communication is fundamental when suggesting treatment. Frequently what is obvious to the dental practitioner, especially with regard to early caries, is not clear to the patient. Dentists rely heavily on sensitivity in the tooth to explain to the patients the need for treatment, but when the tooth is not sensitive, it can be difficult to get patients to move forward with treatment. A patient-friendly device that depicts images of porphyrin collection allows additional patient/dentist communication and provides a more embracive approach to early, preventative treatment procedures. Additionally, plaque and inflamed gums contain high levels of porphyrin which, when monitored weekly, can allow the patient to gauge the quality of their home-care. When used in the dental clinic after prophylaxis, the dentist can use the porphyrin signatures in early-demineralized regions to gauge the success of remineralization therapy or the progress of "watch and see" caries.

An improvement to optical detection of dental decay and gum disease is home monitoring of the porphyrin signal after teeth cleaning (brushing and flossing). Taking measurements at home allow repeated measures over time. These repeated measurements of cleaned tooth surfaces over time is expected to increase specificity of the carious measurement: normal variations in diet and slowly accumulating plaque rate can be accounted for. Trends over time can produce more robust and statistically significant measurements. Single measurements, even after a more thorough tooth cleaning done in the dental clinic, could be expected to produce higher false positive rates and lower specificity.

In order to track the bacterial "hot spots" with heavy or changing porphyrin fluorescence signal, the location of these hot spots must be measured repeatedly over time and mapped with high precision. However, the absolute accuracy or realistic reconstruction of the 3D profile of the teeth and gums does not have to be highly accurate. Even a two-dimensional (2D) representation of the 3D structures is all that is required, as long as the same hot spot location can be found on these flat distorted maps of the 3D structures. Implementation of the hot spot mapping could use 2D maps, or 2D texture maps on surfaces of 3D models that generally represent the teeth, or 3D reconstructions of the person's teeth and gums, or combinations of these approaches. 3D reconstruction from a moving camera is performed using computer vision algorithms, such as structure from motion, or from stereo imaging. Helpful techniques for high reproducibility of the reconstruction will be adding a motion sensor (such as inertia measurement unit) to the wand holding the camera and positioning the camera at a certain distance from the tooth and gum surface, such as a curtain or brush surrounding the camera field of view.

One point of novelty in the optical detection of caries is the unique combination of: (a) quantitative measurement of porphyrin fluorescence, multimodal imaging of reflectance and/or fluorescence of the teeth, creating a 2D or 3D reconstructing these co-registered reflectance and fluorescence images as a camera is scanned across the teeth and gums (possibly having a motion sensor in the wand that houses the camera), repeating these reconstructions of the tooth and gum surfaces over time; and (b) monitoring the attributes of the "hot spots" of porphyrin signal from these reconstructions over time, such as maximum intensity.

One embodiment of a methodology (in chronological order) of such a measurement is listed below. One of ordinary skill in the art will appreciate that fewer, additional, or modified steps may be performed in accordance with the teachings of the present disclosure. First, the porphyrin fluorescence signal may be measured with the autofluorescence background reduced. Next, imaging the teeth and gums may be performed using a moving camera on a wand that scans all the surfaces and reconstructs a 3D surface profile of the teeth and gums. Then, a motion sensor within the wand may facilitate the reconstruction. The distance from the imager (camera) to the teeth can affect the fluorescence signal collected; accordingly, distance compensation may be used to correct for variation in separation distance between teeth and camera. Next, the high intensity regions, or "hot spots," of porphyrin fluorescence can be located in this 3D reconstruction of the teeth and gum 3D surface. These "hot spots" can be tracked over time in repeated reconstructions of the teeth and gums, such as imaging after thorough brushing and flossing every Sunday night. Next, the maximum intensity and area using a full-width at half maximum (FWHM) technique can be measured in each tracked "hot spot" over time, and the rate of change of the hot spot maximum intensity and/or area can be used as an indicator of bacterial loading. Then, each hot spot set of features being measured over time can be compared to all other hot spots, and outliers can be a red flag of more or less disease compared to the average. Any spectral shifts in the fluorescence emission spectrum may be indicative of environmental changes to the bacterial microenvironment (e.g., level of oxygen and pH) and the progression of any disease. Then, machine learning can be used to make the mapping of hot spot measurement in the 2D and/or 3D reconstruction more robust. It is appreciated that in addition to the optical detection of caries and gum disease and its progression (expected increase in porphyrin fluorescence signal over time), this technique can be used to monitor any therapy or healing processes with an expected decrease in the porphyrin signal over time.

A prediction of regions more susceptible to caries and gum disease can be generated by measuring local regions (e.g., hot spots, if associated with porphyrin fluorescence) with more acid buildup (lower pH) after the bacteria are exposed to sugars which can be simply after normal eating. In addition, different rates of increase or decrease of this acid can also be monitored to determine regions of the mouth that are most aberrant compared to a "normal" or an "average bacterial loading." An optical measurement of acid or local pH on the tooth surface and along the gum line can be accomplished by measuring dyes that are classified as pH indicators. These pH indicators will change their fluorescence signal in predictive ways according to the local acidic environment. Fluorescein and its derivatives are pH-sensitive, as well as many molecules in food such as chlorophyll derivatives. Other optical indicators may be used within the body with FDA/IRB approval, such as new dyes, pigments, and particle manufactured by nanotechnology. Porphyrin fluorescence also changes its emission and spectral properties with changes in local pH around the dye molecule. These dyes (fluorescein and porphyrin and their derivatives) can be monitored for spectral shifts by measuring spectral bands of fluorescence emission and/or recording more complete fluorescence emission spectra. By comparing the local pH of all the hot spots of porphyrin fluorescence, some regions that go to lower pH and/or stay longer at low pH may be demineralizing more of the enamel and lead to carious decay faster than other regions. Thus, these regions may be more susceptible to tooth decay or gum disease and these signals can be predictive of such diseases. This proposed monitoring system can use repeated measurements over time and mapping such hot spots to increase sensitivity and specificity of the prediction. In addition to porphyrin and fluorescein, other molecules that are indicative of the metabolic activity, amount, composition, or progression of oral biofilms that are associated with tooth decay and gum disease can also be monitored optically, with or without addition of chemicals, foods, or molecules.

Spectral shifts can be measured by low-cost embedded grating within the wand in front of the camera, or by measuring the light fluorescence from a scanning fiber endoscope (SFE) between imaging frames (typically at a laser wavelength of around 405 nm). Integrating multimodal reflectance and fluorescence imaging and fluorescence spectroscopy measured at the center of the imaging field of view can be done in time series using the scanning fiber endoscope technology.

In one embodiment, imaging is proposed using SFE or camera with narrow bands of illumination/detection. Excitation light is around 405 nm, and detection occurs at three channels (reflectance at 405 nm, blue-green autofluorescence (B/G/AF) of normal teeth at 450-520 nm, and fluorescence of bacterial activity associated with plaque and caries beyond green at 540-560 nm). Camera/SFE detects red fluorescence beyond green, attributed to porphyrins, byproduct of bacterial activity, associated with tooth decay and plaque deposits. In addition to loss of autofluorescence (AF) where caries exists, the B/G AF signal may be used to mitigate AF in the red channel of 580-680 nm. Mitigation of AF crosstalk in the red channel allows for more accurate detection of porphyrin, correlated with the amount of plaque and caries. The 405 nm reflectance signal is used for detecting spots associated with demineralization and caries, and for distance compensation allowing a high degree of quantification of the porphyrin fluorescence to accurately measure plaque and caries. To separate the caries from plaque, video optical images are stitched into mosaics. These mosaics are analyzed for the location of the porphyrin AF signal or reflectance signal that is invisible to the unaided human eye. Gum line locations and at bottom of deep crevasses can be associated with plaque deposits. Deeper locations in teeth that cannot be cleaned off are associated with caries. Application of a dye indicator to a mouthwash or water used for liquid-based flossing may highlight the plaque. This dye can be a food additive or a low-cost FDA approved fluorescence dye such as sodium fluorescein. The use of methylene blue has added advantages of having antimicrobial action when optically excited near its fluorescence excitation max. However, using a dye that is not visible under normal lighting conditions (transparent) would be ideal for cosmetic reasons. Image processing can be on a smart phone, or other personal computer, to monitor therapies with wireless data transmissions.

Intraoral pH sensing based on fluorescence lifetime measurements can be implemented to provide more accuracy. Machine learning methods like linear regression, multi-class classification or deep neural network may be applied to uncover the relationships between caries status and factors including pH recovery rate, resting pH, lowest pH, etc.

Scanning fiber endoscopy (SFE) technology may add robust imaging capabilities at higher performance and at a smaller size than camera-based or point-sensing devices. SFE provides integrated spectrum measurement as well as UV-visible-1R-light imaging for repetitive location-sensitive measurement. By using adaptive and machine vision algorithms to locate the same spots and help guide the user, topical medicine therapy may be applied and monitored accurately at the same location over time.

Another embodiment of an extra function of the devices and methods disclosed here may be to measure saliva flow. Saliva flow is an important factor that may influence the resting pH or pH recovery capability. By measuring saliva flow, additional pathogeny can be identified. At a certain time period after a sugar challenge, a pump may be used to suck saliva from a location and measure the volume. Collected saliva varies by location in the oral cavity (e.g., upper teeth will have less saliva than lower teeth because saliva mostly rests at the bottom of the mouth). An average can be taken as a representation for the overall oral saliva condition, or over-time measurements on each region can be compared and analyzed separately.

To follow is a description of the embodiments described above, and other embodiments not discussed, as they relate to the figures in the instant application.

FIG. 1A illustrates one embodiment a device 100A to anticipate demineralization, in accordance with the teachings of the present disclosure. Device 100 includes laser 101, controller 103, power source 107 (e.g., battery), user interface 109 (e.g., touch-screen, buttons, etc.), fiber optic cable 111, dichroic tube 113 (including beam splitter 115), and spectrometer 121. Also shown is spray bottle 141, which may be filled with a sugar solution 143.

As depicted, light from optical fiber 111 may excite PpIX on the suspicious tooth region with 405 nm laser light from laser 101. A fluorescence signal is then emitted back through fiber optic cable 111. Dichroic filter tube 113 is used to reflect off excitation light and allow the emission light go through the filter (e.g., beam splitter 115) and into spectrophotometer 121. Controller 103 may be coupled to spectrometer 121 to analyze the signal output from spectrometer 121 and control operation of spectrometer 121. A sugar challenge (via sugar solution 143) may be applied by position-specific spray nozzle 141 directed at specific region of the teeth and gums (challenging a single tooth at a time). This may be achieved by attaching a sucking disk to the tip of probe, which can help fix (prevent from moving) the probe.

As shown a light emitter (e.g., laser 101) is coupled to emit an excitation light (here 405 nm, although other wavelengths are contemplated depending on if a dye is used that requires a different excitation energy or the like). The detector (e.g., spectrometer 121) is coupled to receive florescence light produced by a compound in the mouth of the patient in response to the excitation light (depicted as shining on a tooth). Controller 103 (e.g., a general purpose computer, distributed system dispersed across a network, or specialty made computer chip, which may have internal memory such as RAM, ROM, or the like) is coupled to the detector. Controller 103 includes logic that when executed by controller 103, causes system 100A to perform operations such as emitting the excitation light from the light emitter and measuring, over time, an intensity of the florescence light emitted from individual teeth in a plurality of teeth in the mouth. Florescence light may include at least one of 620 nm wavelength light, or 635 nm wavelength light. Controller 103 may then map the intensity of the florescence light emitted from the individual teeth. Controller 103 may also correlate the florescence light emitted from the individual teeth to location of the dental caries. This may be completed using a machine learning algorithm running on controller 103. The machine learning algorithm may include at least one of linear regression, multi-class classification, or a deep neural network.

Here the light emitter (e.g., laser 101) is coupled to a proximal end of fiber optic cable 111, and the excitation light is emitted from the distal end of fiber optic cable 111 opposite the proximal end. It is appreciated that one or more filters (e.g., beam splitter 115) may be positioned to block the excitation light from entering the detector.

It is appreciated that photobleaching, caused by the reaction of fluorophore molecules in the triplet state and dissolved oxygen or other biological molecules, may lead to loss of fluorescer. Lowering excitation energy, or limiting the exposure time of excitation light can reduce photobleaching. In one embodiment, the oral environment may be deoxygenated using anti-oxidative reagents in sugar solution or air spray (e.g., nitrogen gas).

In some embodiments, safety certificated chemicals for fluorescence enhancement and deoxidizing the oral environment may be included in the sugar solution 143. In one embodiment, zinc compounds (such as zinc-acetate) may create a more pH-sensitive PpIX complex. In another or the same embodiment, a pH-sensitive fluorescence (e.g., porphyrin) or optical indicator may physically reside in the oral biofilm indicating the local pH change. In a third embodiment, a spinach extract may be used that generate a greater PpIX amount in the oral biofilm for generating a larger optical signal. No matter what additives are used, the whole process for users includes repeated measurements over time, such as "measure-spray-measure-wait-measure-wait-measure . . . ."

Figure 1B:
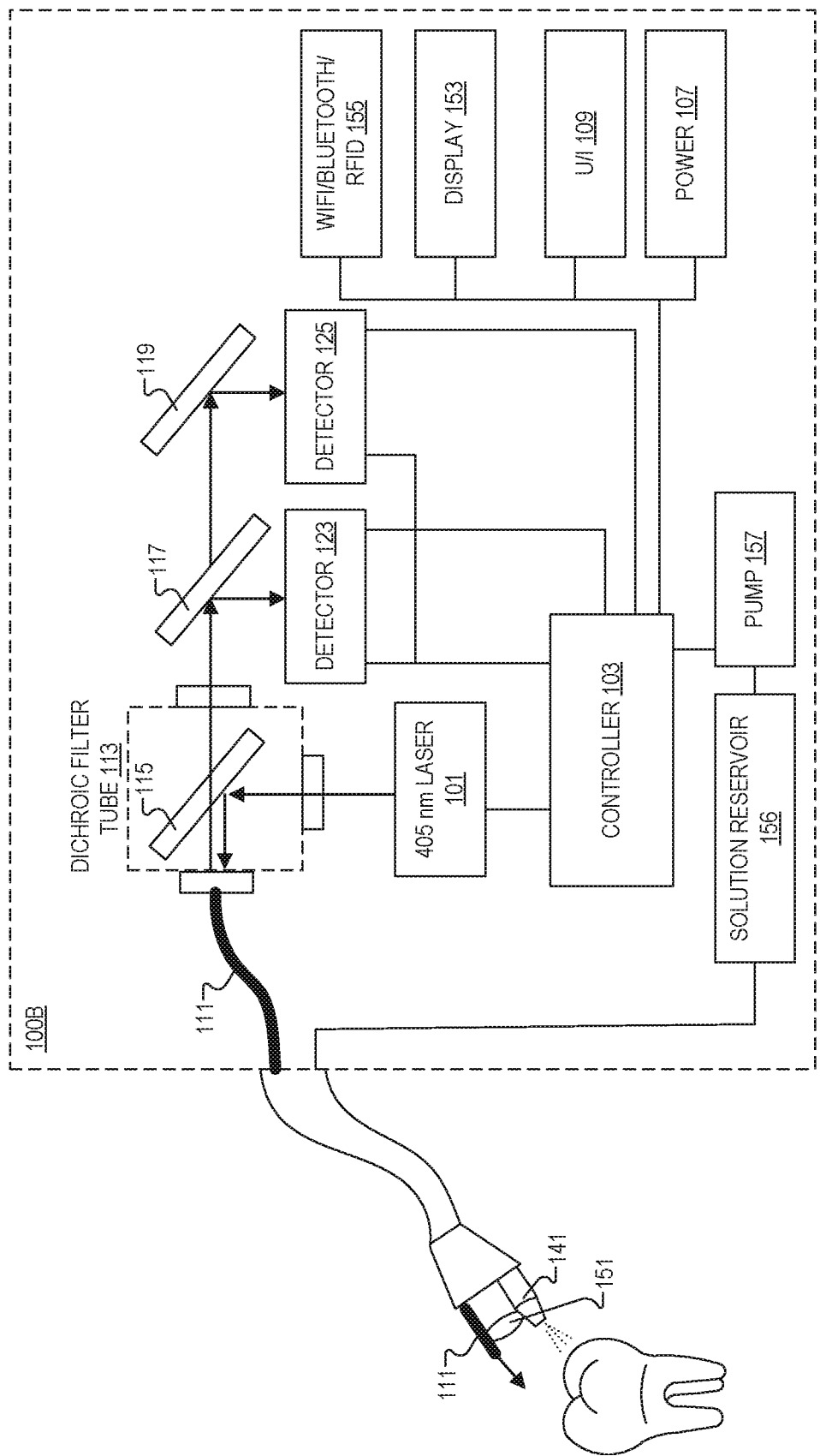
FIG. 1B illustrates another embodiment of a device to anticipate demineralization, in accordance with the teachings of the present disclosure.

FIG. 1B illustrates another, more complex, embodiment of a system 100B to anticipate demineralization, in accordance with the teachings of the present disclosure. System 100B includes many of the same features as system 100A of FIG. 1A. However, system 100B includes fiber bundles 111 (with return fibers surrounding the center illumination fiber to increase the signal), a first detector 123, a second detector 125, a first beam splitter 117, a second beam splitter 119, a display 153, a wireless emitter and receiver 155 (e.g., Bluetooth, wireless, RFID or the like), an image sensor 151, a solution reservoir 156 and a pump 157.

In the depicted embodiment, the light emitter (e.g., laser 101), the detector (e.g., detectors 123 and 125), and controller 103 are disposed in a housing, and solution reservoir 156 is also disposed within the housing and positioned to spray a sugar solution on the plurality of teeth. The sugar solution may be pumped out of the housing with pump 157, and in response to the press of a button or the like. Pump 157 may receive power from power supply 107, which may include a battery, power outlet, inductive charging coil or the like.

Fiber bundle 111 includes return fibers that improve collection efficiency of the return light while only slightly increasing the size of the probe. The probe (e.g., the distal end of fiber bundle 111 with nozzle 141) may include camera 151 (e.g., with lens optics and a CMOS image sensor or the like) to image teeth structures and fluorescence locations to help users identify higher fluorescence intensity or "hot spot" of plaque and orient probe to target. In place of a separate spray nozzle, an adjustable dental nozzle that can extrude fluids and possibly withdraw fluids from the distal end may be integrated to the probe. In the depicted embodiment, the spectrophotometer is replaced with filters (e.g., beam splitters 117 and 119 depicted here) and detectors 123 and 125. Generally, only intensities of two wavelengths are needed for a robust optical pH measurement through intensity ratio-metric method. Furthermore, controller 103 (which may include chip-based technologies such as general purpose processor, or a processor specifically designed for this application coupled to memory such as RAM, ROM, or the like) can replace a computer to control the triggering of light source 101 and the receipt/analysis of data. Wireless emitter and receiver 155, such as Bluetooth or a wifi module, may be embedded in the microcomputer system (e.g., controller 103) to transmit data to the home computer of the dental clinic for remote monitoring and treatment guidance. For example, some simple treatments that can be completed by patients with a dentist's remote guidance may not require an office visit.

The oral probe (e.g., the distal end of fiber bundle 111 with nozzle 141 and camera 151) may be supported by a semi-rigid shaft, which can have a hood to restrict the fluid flow within the range of the tooth surface that's being measured and maintain a certain distance from the distal end of the probe and the surface of the teeth and gums. The probe shaft can be adjusted (e.g., bent) in its shape by applying some force so that measurement can be taken in various locations, while being able to stay in its shape stably during a hand-held measurement. Fiber bundle 111 and a spray nozzle 141 are co-localized in the probe. Fiber bundle 111 and spray nozzle 141 can be fixed next to each other so that there is minimum spatial lateral offset. In another embodiment, fiber bundle 111 may be mounted in a hollow tube in a coaxial way so that the sugar challenge and measurement can be taken concurrently or in a rapid time series. In some embodiments, fiber bundle 111 can be replaced with a scanning fiber endoscope (SFE) probe or a toothbrush-like wand. In another embodiment, there may be the capability to extend out further and draw back in an axial manner, which can be adjusted by piezoelectric actuators. In the sugar challenge step, the spray nozzle 141 can extend out while fiber bundle 111 is withdrawn into a cavity so that it will not be contaminated by the sugar solution. In the measurement step, fiber bundle 111 may extend out to get closer to the tooth surface while spray nozzle 141 is drawn back to allow more space. This way, the user needs to move the probe between two stages but the minimal size of the apparatus should allow the user to adjust rapidly. For application in a dentist's office, a disposable cover may be wrapped around the probe without blocking camera 151, fiber bundle 111, and nozzle 141. Standard cleaning procedures like rinsing with alcohol may be used on the fiber bundle 141 and lenses in camera 151. For the sake of convenience, a transparent disposable cover may be used to cover the fiber bundle 151 and the lens of camera 151 without influencing imaging. Auto fluorescence of the cover can be subtracted from the signal as background. Either way, spray nozzle 141 can be renewed between uses.

The imaging light is collected close to the illumination fiber used for excitation. Camera 151 (e.g., a CMOS or CCD sensor) will collect light from the illuminated spot on the teeth or gums. Two functions may result from this embodiment: taking 2D images of teeth surfaces with enhanced fluorescence or a reflection signal, and collecting fluorescence or reflection signal from the optically excited region. These two functions of imaging and fluorescence spectroscopy may be combined using the same instrument, such as the scanning fiber endoscope (SFE). The intensity of the florescence light emitted from the individual teeth may be mapped onto the images of the individual teeth that were captured. In some embodiments it is appreciated that image sensor is included in the detector, or may even function as the detector (e.g., if filtering algorithms or color filters are used to distinguish between different wavelengths of light).

2D images with enhanced fluorescence or reflection signal may be used to identify locations of all suspicious regions in the oral cavity. They may also be used to create 3D reconstructions for the display of bacterial accumulation of porphyrin or plaque loading on the teeth, gums, and other soft tissues. 3D reconstruction from the moving camera 151 may be performed using computer vision algorithms, such as edge detection, stereo imaging, visual hull method, and/or structure from motion. Helpful techniques for high reproducibility of the reconstruction can be integrated such as an inertia measurement unit, measuring the diffuse reflectance signal to compensate for variable distance from the probe tip to the teeth or gums, or physically maintaining the light collection at a certain distance from the tooth and gum surface, such as maintaining contact of a curtain or brush surrounding the camera field of view. Another embodiment of 3D reconstruction is collecting feature points on the tooth surface using edge/feature detection algorithms, so that a sparse 3D point cloud of the tooth surface can be constructed. Then applying machine learning algorithms to reconstruct the complete 3D model by using 3D-encoder-predictor convolutional neural network for shape synthesis. One more embodiment of 3D reconstruction may include collecting multiple frames around the tooth at multiple perspectives, and applying machine learning to recover the 3D model from the sequence of images.

Camera 151 may also make sure the same spot can be repetitively located during multiple measurements over time. As shown in FIG. 2, after the first measurement, coordinates are generated from the edges and point features are extracted from the reflection image of tooth structure and then saved (e.g., image 201 showing extracted image points). Then after every time the measurement is repeated, the initial coordinate is displayed on the user interface as contours and feature points (e.g., image 203). Once the user orients the probe so that the real-time image matches with the saved coordinates, the system informs user by lighting up an LED or beeping and then allowing the user to make the measurement. A clamping device can also be designed to fix the probe onto teeth so that user does not need to try to stabilize the probe or use precise hand control.

Figure 3:
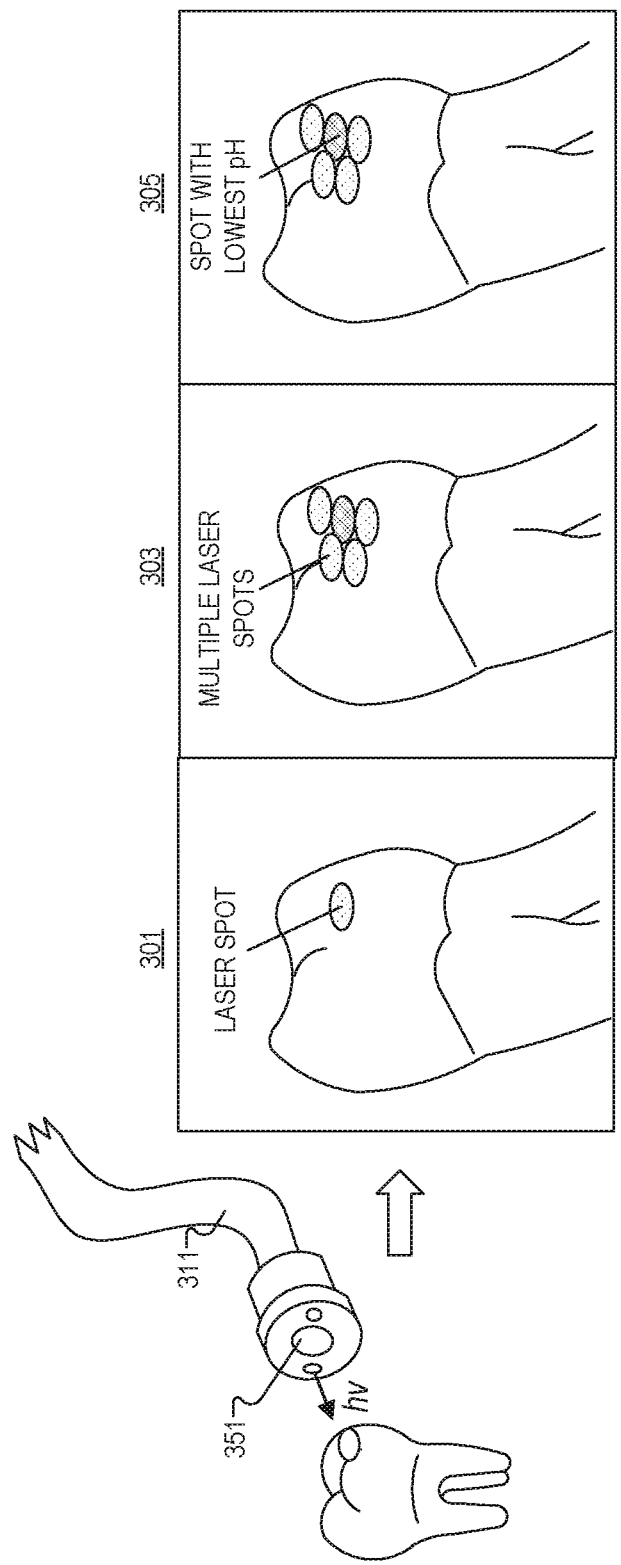
FIG. 3 illustrates an embodiment of pH mapping, in accordance with the teachings of the present disclosure.

To compare severity of different suspicious regions, the fluorescence or phosphorescence signal may be measured on a certain point (small area). FIG. 3 depicts this method to map the pH results over suspicious regions, and then the area with lowest pH can be located. The location that is correlated with the most persistent acidic local environment may represent the greatest cariogenic severity, which, in terms of the fluorescence or phosphorescence signal, would have the maximum change in the optical spectra as a function of pH. Creation of a 3D spatial map of the teeth for pH mapping may only need to be done in the first measurement. After the area of interest is located and mapped, the tooth structural features from the reflection image will be saved for guiding future re-measurement of pH at the same location.

As shown in the embodiment in FIG. 3, camera sensor 351 may be used to emit light (hv) and capture the reflection and fluorescence signal from an excited spot. Block 301 depicts shining the laser light on a spot on the tooth. As depicted in block 303-306, by moving the apparatus over the suspicious region, the area is scanned (manually or automatically) and the spot with the maximum fluorescence intensity spectral shift with respect to pH change can be selected.

To measure all hot spots, there are two primary methods. The first method includes measuring changing pH curves simultaneously on all hot spots after a thorough sugar rinse, swishing around the sugar solution in the oral cavity. To account for the time to measure all suspicious spots in series, two series of measurements will be taken for all suspicious regions, with the second in the series being in reverse order from the first, as shown in FIG. 4. This helps to minimize the influence from the order of measurements taken over a period of time. FIG. 4 shows an embodiment of numbering all suspicious regions in oral cavity after initial imaging inspection (e.g., 401) and measuring Stephan curve of all suspicious regions after a thorough sugar rinse (e.g., 403): ranking of different regions by averaging two sets of measurement in reverse orders. For example, 10 minutes after sugar challenge, the user may start to take pH values from #1 to #32 suspicious region, which may take around 7 minutes; then immediately take another 7 minutes of pH measurements in reverse order, from #32 to #1. Since the Stephan curve is approximately linear during these time periods, then the average of the two values is calculated from two pH measurements at each region, which ideally should be the pH value at about 7 minutes on average after the sugar challenge. Non-linear relationships of pH recovery after sugar challenge can also be factored into the average pH measurement to prove relative measures among suspicious regions. A whole set of measurements would take 14 minutes, which enables the measurement of resting pH and pH recovery rate. However, it is difficult to measure the minimum pH since measurement of each time point takes a period of time. Another method then is to apply sugar challenge locally by covering the probe with some shield and rinsing the oral cavity with water after measurement. Then for each hot spot, the sugar challenge is applied and the signal measured separately. The minimum pH can be measured by finding the minimum pH value from a series of measurements.

Figure 5:
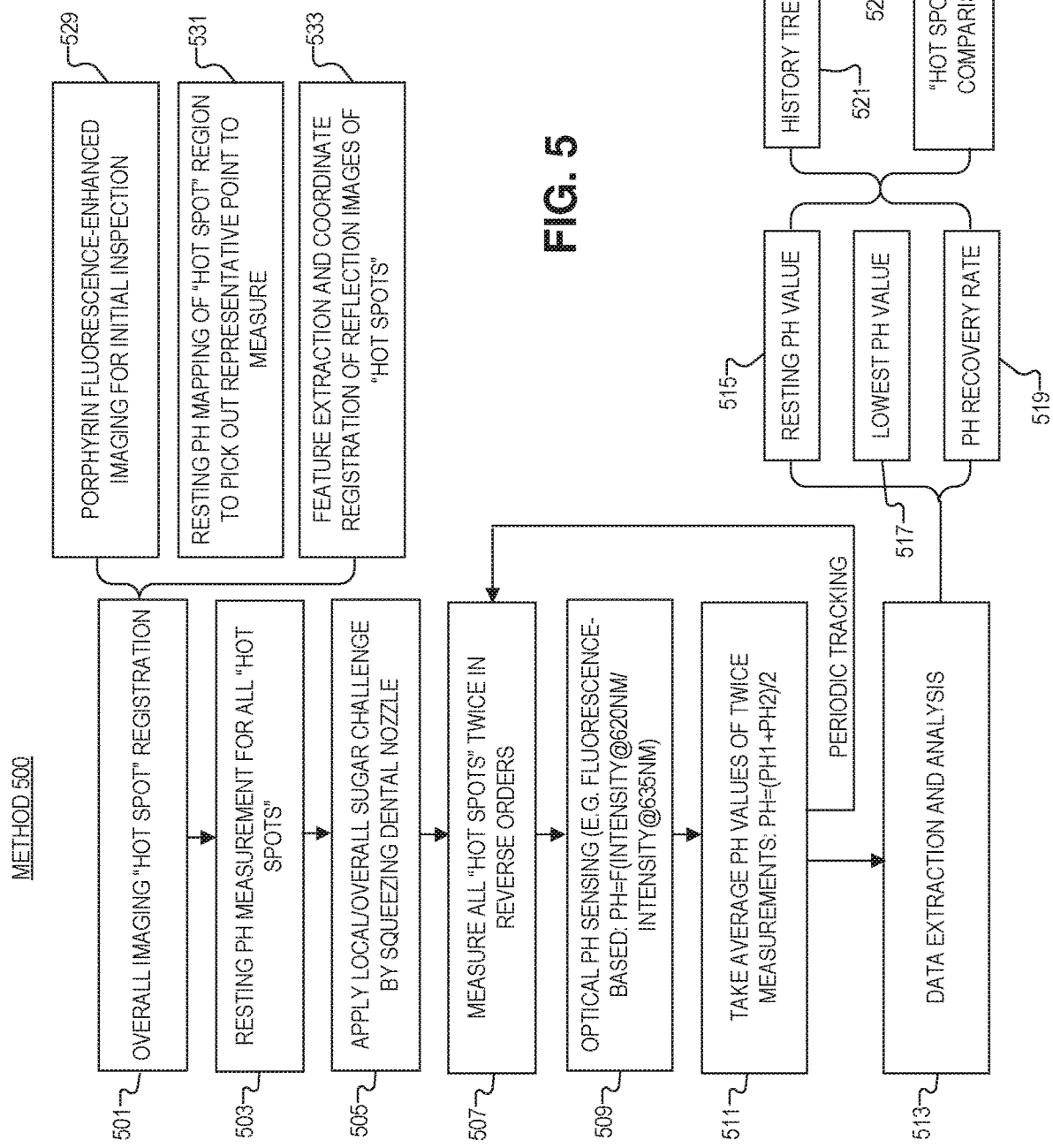
FIG. 5 is a flow chart illustrating one embodiment of a method to image hotspots, in accordance with the teachings of the present disclosure.

FIG. 5 is a flow chart illustrating one embodiment of a method 500 for pH measurement and registration of hot spots and caries prediction and ranking of these hot spots, in accordance with the teachings of the present disclosure. Method 500 is an embodiment of one way to implement the processes described above. One of ordinary skill in the art having the benefit of the present disclosure will understand that blocks 501-533 in method 500 may occur in any order and even in parallel. Further, blocks may be added to, or removed from, method 500, in accordance with the teachings of the present disclosure.

Block 501 depicts over all imaging hot spot registration. It is appreciated that this block may include the processes depicted in blocks 529-533. More specifically, porphyrin fluorescence-enhanced imaging for initial inspection (block 529), resting pH mapping of hot spot regions to pick out representative points to measure (block 531), and feature extraction and coordinate registration of reflection images of hot spots (block 533).

Block 503 depicts conducting resting pH measurements for all hot spots. Then block 505 depicts applying either a local or over-all sugar challenge, which may be accomplished by squeezing a dental nozzle (e.g., on the device depicted in FIG. 1B to dispense fluid from the fluid reservoir).

After applying the sugar, block 507 illustrates measuring all hotspots twice in reverse order. For example, 32 teeth may be measured. First teeth 1-32 are examined for hotspots, then teeth 32-1 are examined for hotspots. Block 509 shows this may be accomplished through optical pH sensing; more specifically by looking at the relative intensity of fluorescence light at 620 nm and 635 nm. Then, in block 511, the average pH for each of the teeth is calculated using the equation $pH=(pH1+pH2)/2$, where pH is the average pH of the tooth over the two measurements, pH1 is the first pH measurement, and pH2 is the second pH measurement. These steps may occur iteratively to produce periodic tracking.

In block 513, data may be extracted from the device and various metrics may be calculated, plotted, or graphed. For example, in block 515 the resting pH is calculated. In block 517 the lowest pH value is calculated. In block 519 the pH recovery rate is calculated. In block 521 the historical trend is calculated or plotted, and in block 523 the hotspots are ranked. Using this information, a machine learning algorithm or the like may predict where hotspots are likely to occur (block 525), and/or the teeth are ranked with respect to the amount of bacteria or carries as measured via optical pH measurement.

Figure 6:
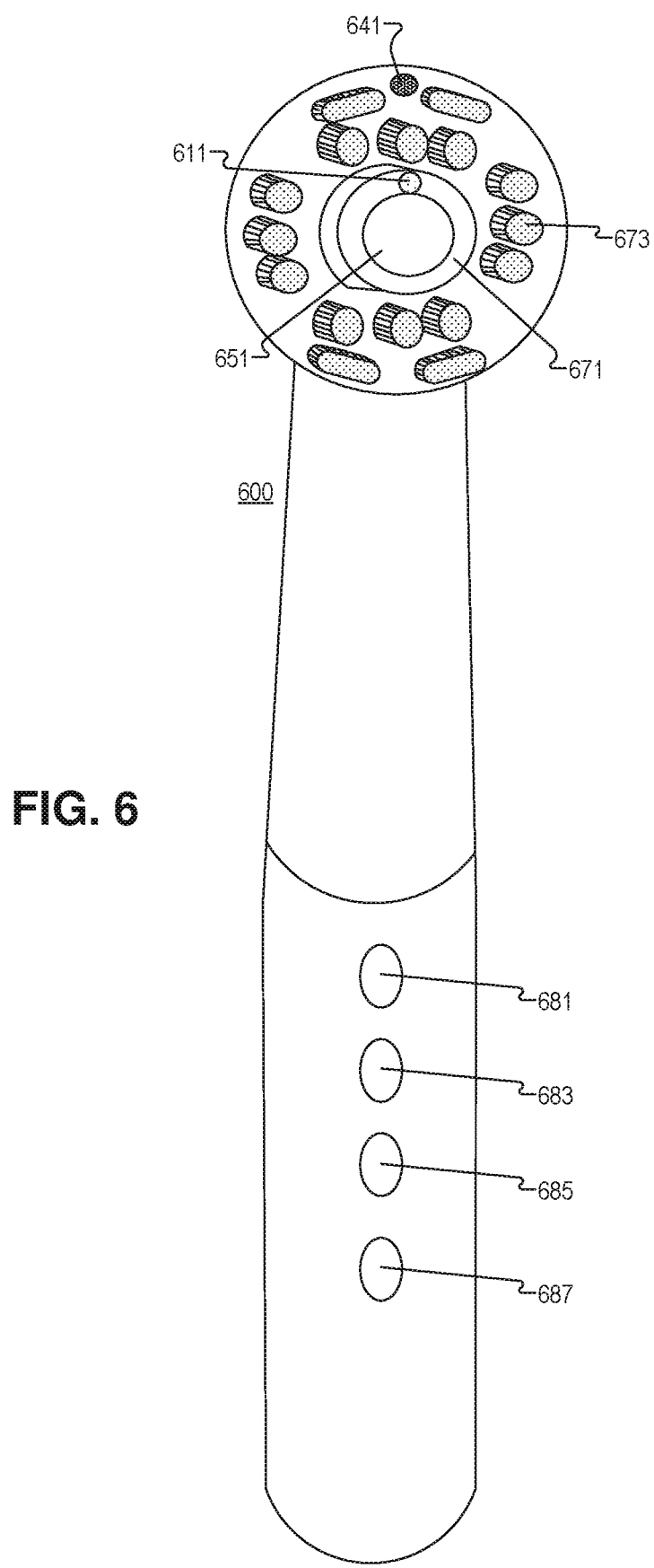
FIG. 6 shows a toothbrush-like device having integrated caries detection functionality, in accordance with the teachings of the present disclosure.

FIG. 6 shows part of a toothbrush-like device 600 having integrated carries detection functionality, in accordance with the teachings of the present disclosure. As shown, device 600 includes optical fiber 611, camera 651, rubber camera housing 671, spray nozzle 641 (to dispense the sugar solution), bristles 673, and buttons 681-687. Device 600 may be an electric toothbrush with oscillating head functionality that also may be used to detect caries. Other components such as power supply, controller and the like may be integrated into the handle/housing of device 600.

In the depicted embodiment, buttons 681-687 may be light activated (e.g., via a photodiode); when a user gently puts his/her finger above the button, the sensor will sense it and implement certain operations. This will avoid the influence on measurement from moving and pushing. The system may beep or vibrate again once the measurement is done. Similar button control can also be implemented on touch screens. Controls may also be implemented with a foot pedal or voice recognition and activated by such. In the depicted embodiment, button 681 activates a rinse solution channel with water, button 683 activates the pump solution channel, button 685 applies the sugar solution, and block 687 takes the optical pH measurement.

Figure 7:
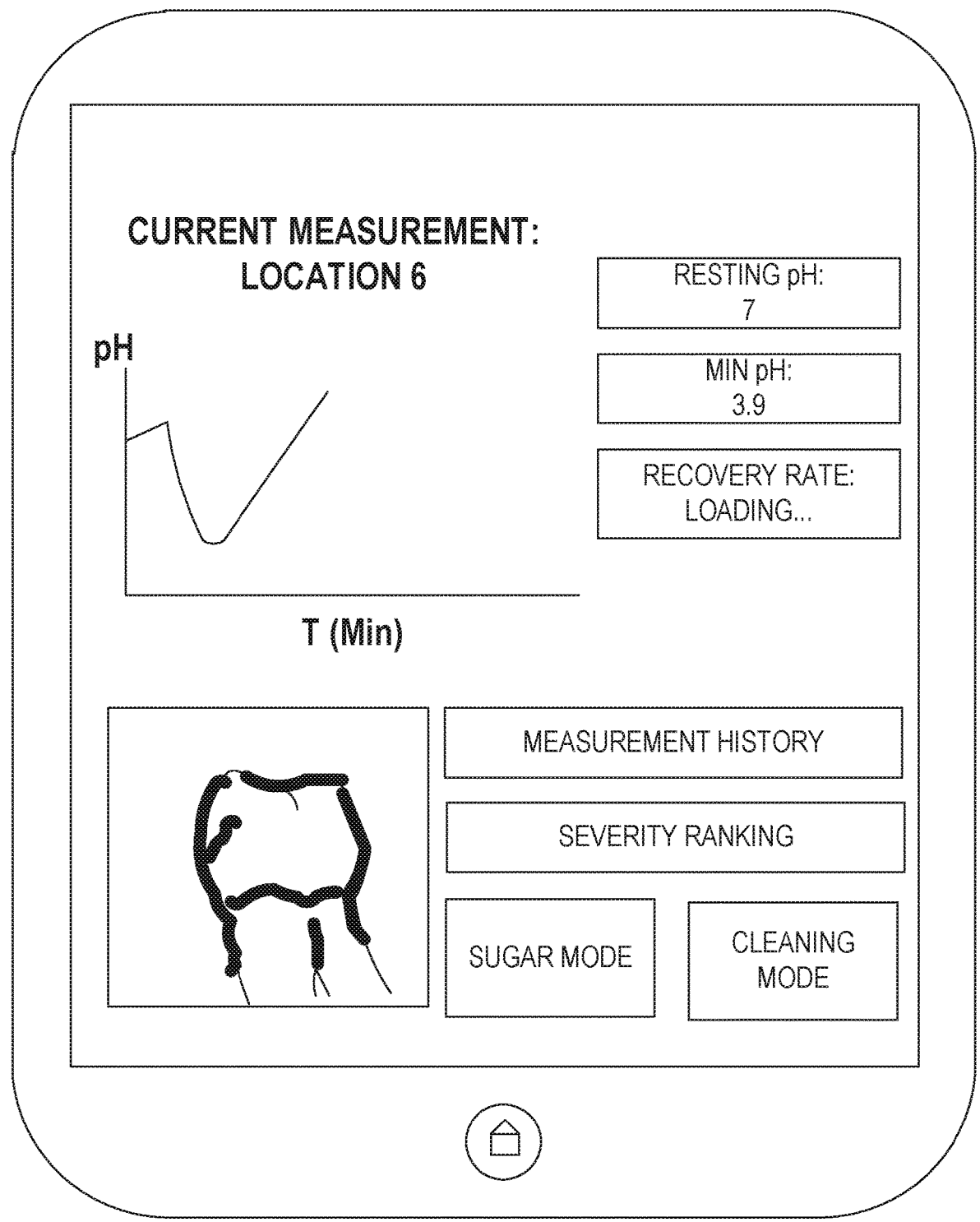
FIG. 7 depicts an embodiment of a user interface for the detection and measurement of caries, in accordance with the teachings of the present disclosure.

FIG. 7 depicts an embodiment of a user interface 700 for the detection and measurement of caries, in accordance with the teachings of the present disclosure. As shown, data collected from a measurement device (e.g., the device depicted in FIGS. 1A and 1B) may be sent to a tablet, or other general purpose computer for a better visualization experience. As shown, images of the tooth being measured are presented to the user, along with real-time data. The data collected may be plotted. Moreover, the data may be displayed and parsed any number of ways using different user interface screens. An embodiment of the user interface contains the display screen and the handle that supports the measurement probe or toothbrush-like wand. Display of real-time images from the camera may help the user to orient the probe to the desired position. Current data taken on certain hot spots will be displayed and plotted in near real-time on screen. Important parameters such as resting pH, minimum pH and recovery rate are also extracted from the curve and displayed on the screen. Systems that measure time after the sugar spray may remind the user to take measurement by beeping or flashing an indicator light. Historical measurements on each hot spot with the trend of resting pH, minimum pH and recovery rate can be displayed or looked up so that users can monitor the effect of their hygiene (such as brushing and flossing) or medical therapy. Extra data processing may be performed to eliminate variance of data. Severity ranking shows the data of all hot spots measured at a particular time period, and can rank them in terms of severity of different parameters or combination of parameters.

Figure 8:
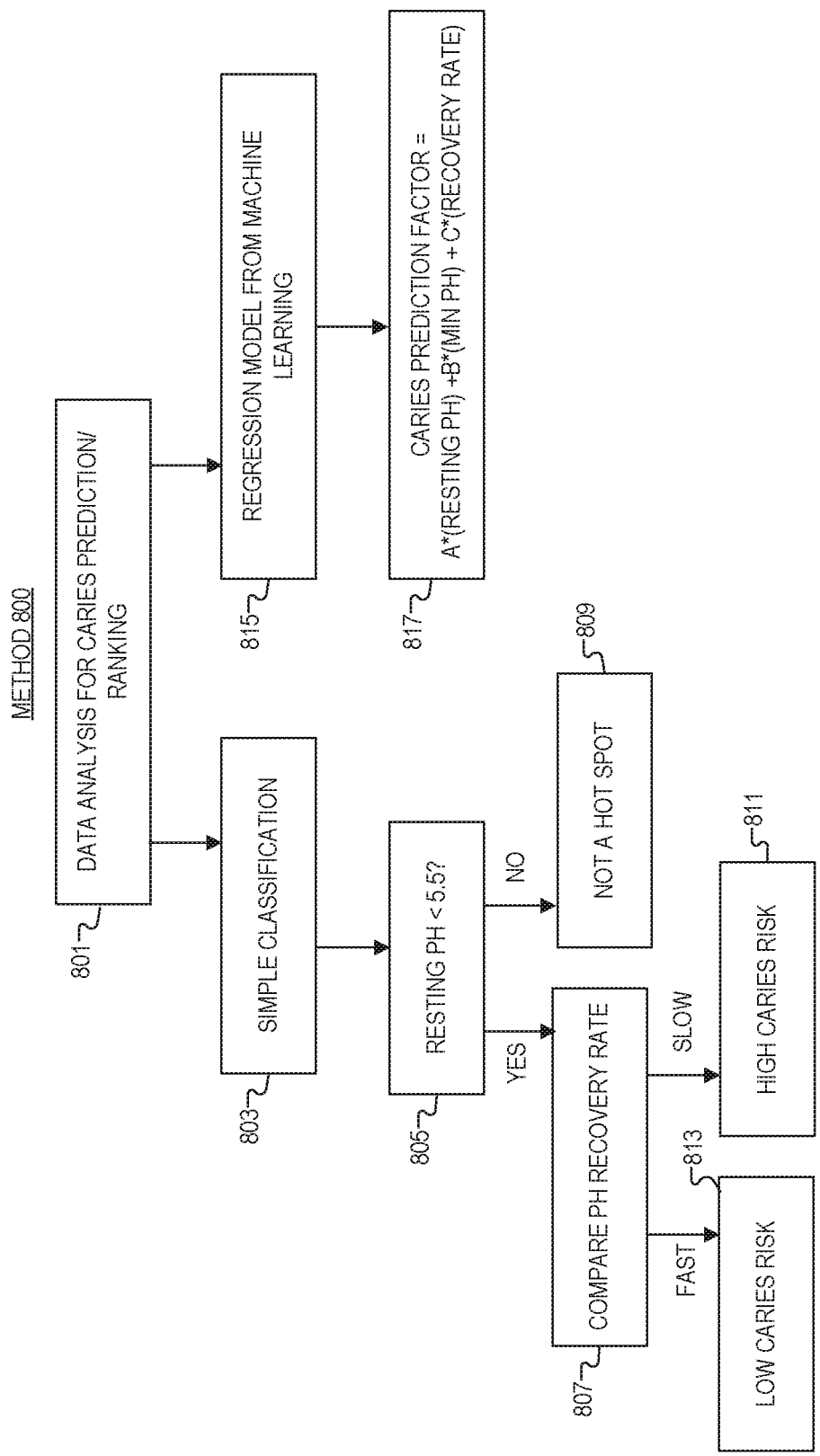
FIG. 8 depicts an embodiment of post-analysis methods to predict caries risk, in accordance with an embodiment of the disclosure.

FIG. 8 depicts embodiments of post-analysis methods 800 to predict caries risk, in accordance with an embodiment of the disclosure. One of ordinary skill in the art having the benefit of the present disclosure will understand that blocks 801-817 in method 800 may occur in any order and even in parallel. Further, blocks may be added to, or removed from, method 800, in accordance with the teachings of the present disclosure.

Blocks 803-813 depict a straightforward way to classify severity and rank suspicious regions using two parameters: resting pH value, and pH increasing rate after sucrose challenge. The first screening is completed by finding all regions with resting pH values lower than 5.5 (block 805) which is considered to be the line under which demineralization occurs. After a sucrose challenge, the low pH will return to the local resting pH. Areas with more active cariogenic bacteria would return to resting pH slower (block 811), leading to longer periods of demineralization (increased caries risk). Areas with less bacteria activity will return to the resting pH faster, indicating a lower caries risk (block 813). Thus the ranking will be calculated considering both resting pH and rate that the pH returns to the resting pH.

Blocks 815-817 illustrate a more complex learning algorithm which may use a combination of parameters to classify caries, such as data generated over time on the same oral cavity. Furthermore, machine learning algorithms may be used to provide better regression and classification results. For example, the formula depicted in block 817 (a*(resting pH)+b*(min pH)+c*(recovery rate)) may be used to reliably distinguish severity/risk of suspicious regions. The regression fitting can be trained using machine learning algorithms to provide optimal model.

Figure 9:
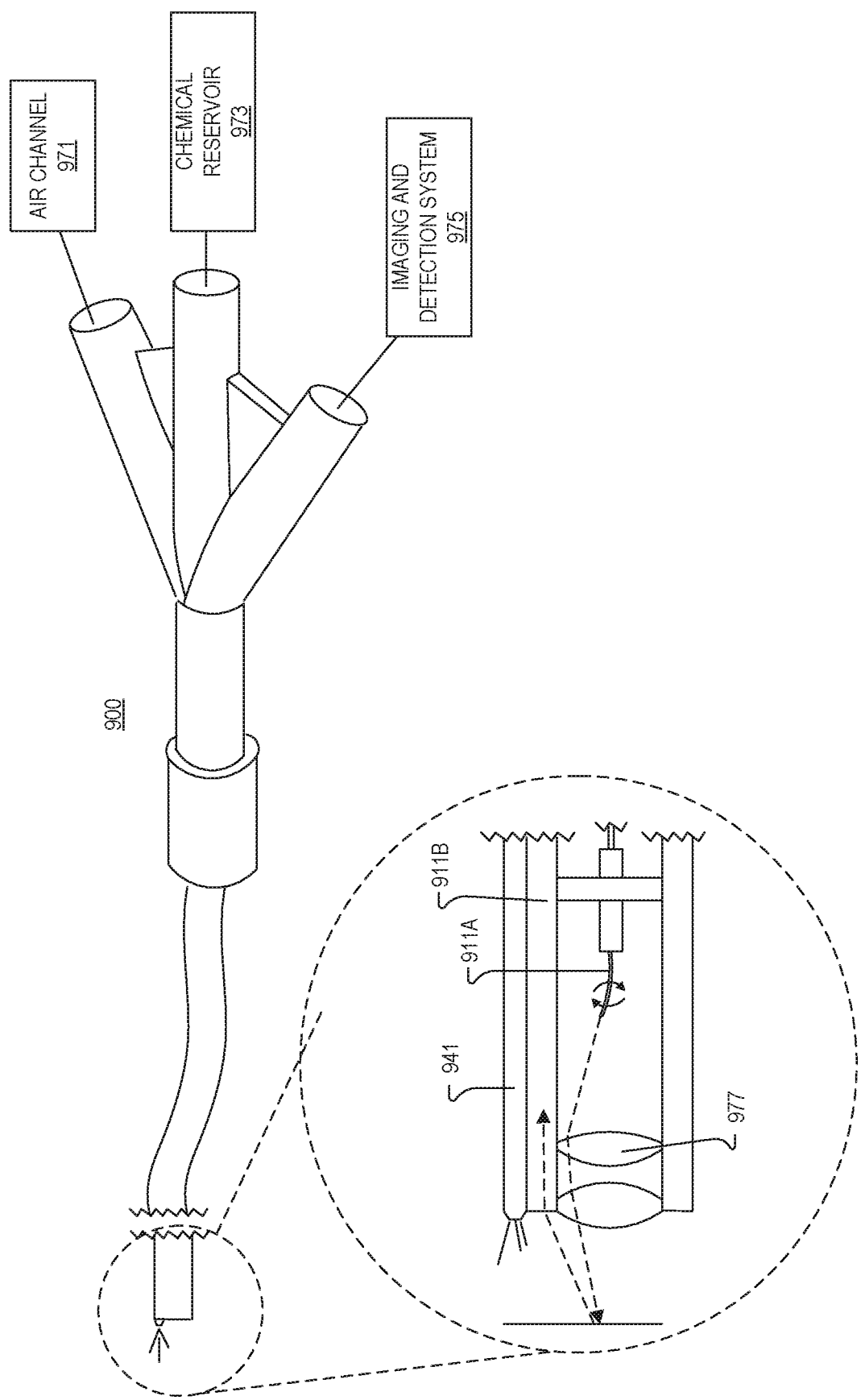
FIG. 9 depicts an embodiment of a measurement probe based on scanning fiber endoscope technology, in accordance with the teachings of the present disclosure.

FIG. 9 depicts an embodiment of a measurement probe 900 based on scanning fiber endoscope (SFE) technology, in accordance with the teachings of the present disclosure. Coaxial measurement probe 900 includes air channel 971 (to press the chemical-sugar-solution out), chemical solution reservoir 973, and imaging and detection system 975. Also depicted is the tube portion of the endoscope with the distal end magnified. The distal end includes scanning fiber 911A, and light return fiber 911B, spray nozzle 941 (to dispense the sugar solution), and lens optic 977 (to focus the emitted light). SFE technology provides real-time wide-field of view by scanning optical fiber 911A with a cantilever by generating a near-resonant vibration induced by piezoelectric actuator. Due to the small tip diameter and flexible fiber shaft of optical fiber 911A, the device can reach into small crevices to take images. Integrated reflectance images combined with an enhanced fluorescence signal allows SFE to replace the camera and fiber bundle discussed in former embodiments while decreasing the footprint of the probe. Such probe can be integrated into a toothbrush-like device (see e.g., FIG. 6). Furthermore, it can be combined with a dental nozzle in a coaxial manner. Sugar solution will be sprayed through nozzle 941 surrounding the centered SFE probe. Water rinse after the sugar challenge can clean the probe tip so that the lens is not contaminated or the image blurred. Spectral shifts can be measured by measuring the light fluorescence from the scanning fiber endoscope between imaging frames.

Figure 10:
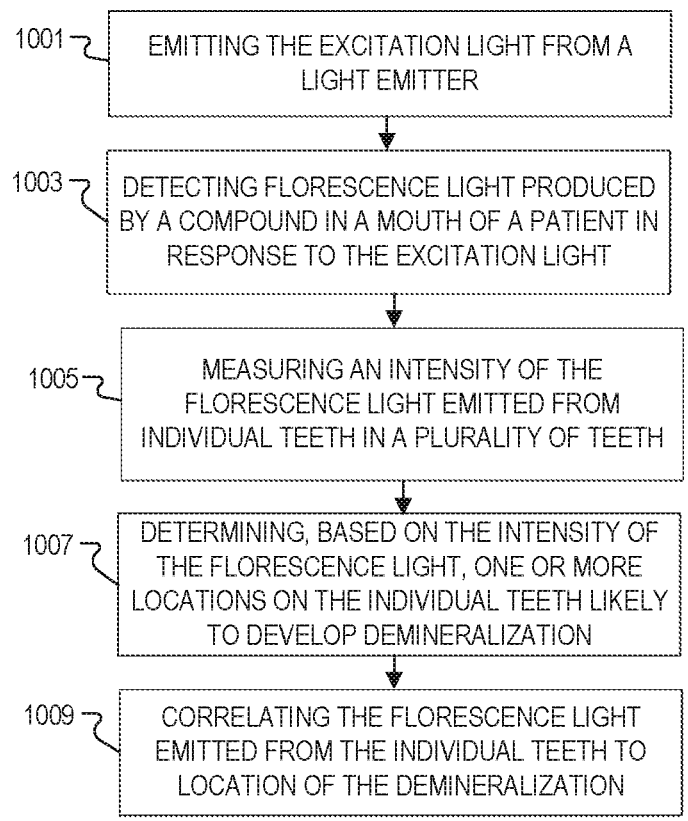
FIG. 10 illustrates a method for the optical detection of dental caries, in accordance with the teachings of the present disclosure.

FIG. 10 illustrates a method 1000 for the optical detection of dental caries, in accordance with the teachings of the present disclosure. One of ordinary skill in the art having the benefit of the present disclosure will understand that blocks 1001-1009 in method 1000 may occur in any order and even in parallel. Further, blocks may be added to, or removed from, method 1000, in accordance with the teachings of the present disclosure.

Block 1001 shows emitting the excitation light from a light emitter. In some embodiments, before testing begins, a sugar solution may be applied to the mouth of the patient. In some embodiments, emitting the excitation light from a light emitter is in response to the patient pressing a button on a housing that includes the light emitter, the detector, and the controller.

Block 1003 illustrates detecting, with a detector, florescence light produced by a compound in the mouth of a patient in response to the excitation light. In some embodiments, the compound may include porphyrins or dye molecules added to the mouth of the patient.

Block 1005 depicts measuring, using a controller coupled to the detector, an intensity of the florescence light emitted from individual teeth in a plurality of teeth, and the intensity is measured over a period of time. In some embodiments, the excitation light may be filtered from the florescence light prior to receiving the florescence light with the detector.

Block 1007 shows determining, based on the intensity of the florescence light, one or more locations on the individual teeth likely to develop demineralization. This may include mapping the intensity of the florescence light emitted from the individual teeth. For example, the florescence light on images of teeth (e.g., with the fluorescing portions overlaid on the teeth on a display), or recording the coordinates of florescence on a 3D or 2D model of the patient's mouth. Alternatively or additionally, the locations of florescence may simply be recorded ("mapped") in a table or a graph.

Block 1009 illustrates correlating, using the controller, the florescence light emitted from the individual teeth to locations of the demineralization. In one embodiment, this is achieved by using a machine learning algorithm running on the controller to determine the locations of the dental caries. It is appreciated that the machine learning algorithm may include at least one of linear regression, multi-class classification, or a deep neural network. The machine learning algorithm correlates spectral shifts in the florescence light to a location of the dental caries (e.g., where there is a high concentration of bacteria emitting florescent chemicals, there is a high concentration of caries). Further, the system performing method 1000 may capture images of the individual teeth using an image sensor (e.g., a CMOS sensor) coupled to the controller, and map the intensity of the florescence light emitted from the individual teeth on the images of the individual teeth.

FIGS. 11A-11B illustrate successful experimental results of the techniques described herein, in accordance with the teachings of the present disclosure. Specifically, FIG. 11A shows a graph of Chlorin ($C_{34}H_{33}N_4Na_3O_6$) in buffer solution. Solution preparation includes: 4 uM chlorin in chemically defined media (CDM) buffered at 3.7, 4, 5, 6, and 7 pH. The measurement and analysis includes: Placing 300 uL each of the five chorin buffer solutions in a 24 well sterile clear plastic plate, including one CDM solution with no chlorin. Exciting the solutions with a 3 mW 405 nm laser and recording fluorescence spectra with an Ocean Optics USB200+ spectrometer. The collected spectral data was transferred to Microsoft Excel, and the background fluorescence spectra of the CDM (without chlorin) was subtracted from all other spectral measurements. The ratio was calculated and the 640 and 680 nm fluorescence intensity values were plotted from each plaque spectra with respect to buffer pH.

FIG. 11A also shows a 515/580 nm fluorescence ratio graph. Molecular formulas of the substances used include Fluorescein sodium salt: $C_{20}H_{10}Na_2O_5$; and Rhodamine B: $C_{28}H_{31}ClN_2O_3$. Solution preparation includes: 20 uM fluorescein sodium salt and 20 uM rhodamine B in chemically defined media (CDM) buffered at 3.7, 4, 5, 6, and 7 pH. Measurement and Analysis includes: placing 300 uL each of five fluorescein/rhodamine B buffer solutions in a 24 well sterile clear plastic plate, including one CDM solution with no fluorescein/rhodamine B. Exciting the solutions with a 3 mW 405 nm laser and record fluorescence spectra with an Ocean Optics USB200+ spectrometer. Transferring the spectral data to Microsoft Excel and subtracting the background fluorescence spectra of the CDM without fluorescein/rhodamine B from all other spectra measurements. The ratio was calculated and 515 and 580 nm fluorescence intensity values from each plaque spectra with respect to buffer pH were plotted.

FIG. 11B shows the results of a sucrose challenge with measuring plaque pH optically in vitro. The molecular formulas of the compounds used are Fluorescein Sulfonic Acid: $C_{20}H_9Na_3O_8S$; and Rhodamine B: $C_{28}H_{31}ClN_2O_3$. Solution preparation includes: Obtaining human plaque from a volunteer who did not brush for 24-36 hours prior to collection. Measurement and Analysis includes: scraping plaque from the subject's teeth, and placing the plaque into Eppendorf tubes filled with 250 uL CDM 7 pH. The plaque is centrifuged at 200 RPM for 4 minutes and then mixed the thoroughly. Then all supernatant is transferred into a well of a 24 well sterile clear plastic plate and add 120 uL 0.1 mM rhodamine B, and 375 uL DI water to the tube. The well is mixed, and then 300 uL of plaque solution is transferred into another well of the 24 well plate. 42 uL 0.42 mM fluorescein sulfonic acid is added, along with 10 uL 0.156 M of sucrose. The pH and fluorescence spectra of the supernatant are measured. The solutions were excited with a 2 mW 405 nm laser and fluorescence spectra was recorded with an Ocean Optics USB200+ spectrometer. The spectra of the plaque were measured (10 avg) at 1 minute intervals, mixing the well before measurements. Calibration measurements were performed with europium standards (0.18 and 0.5 ppt concentrations). Measuring the pH of the well at 10 minute intervals after the pH drop slows, which is about 10 minutes after sugar addition. The spectra data was transferred to Microsoft Excel. The background fluorescence spectra of the supernatant is subtracted from all other spectra measurements. The ratio is calculated and 515 and 580 nm fluorescence intensity values from each plaque spectra are graphed with respect to time.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application-specific integrated circuit ("ASIC") or otherwise. Processes may also occur locally or across distributed systems (e.g., multiple servers).

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated examples of the invention, including what is described in the Abstract, is not intended to be exhaustive or to limit the invention to the precise forms disclosed. While specific examples of the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific examples disclosed in the specification. Rather, the scope of the invention is to be determined entirely by the following claims, which are to be construed in accordance with established doctrines of claim interpretation.

The embodiments of the invention in which an exclusive property or privilege is claimed are defined as follows:

1. A system for the optical measurement of pH, comprising:
   a light emitter to emit an excitation light;
   a detector configured to receive, in response to the excitation light, florescence light produced by a pH-sensitive compound when the pH-sensitive compound contacts one or more surfaces of individual teeth; and
   a controller coupled to the detector and the light emitter, wherein the controller includes logic that when executed by the controller, causes the system to perform operations including:
   emitting the excitation light from the light emitter;
   performing a series of measurements over a period of time, each measurement included in the series of measurements measuring an intensity of the florescence light emitted from the pH-sensitive compound when the pH-sensitive compound contacts the one or more surfaces of the individual teeth;
   correlating the intensity of the florescence light to a pH proximate to the one or more surfaces of the individual teeth for the series of measurements to determine at least one of a resting pH, a minimum pH, or a pH recovery rate proximate to the one or more surfaces of the individual teeth; and
   determining, based on at least one of the intensity of the florescence light the resting pH, the minimum pH, or the pH recovery rate, one or more locations on the individual teeth likely to develop demineralization.

2. The system of claim 1, wherein the one or more locations on the individual teeth likely to develop demineralization have a lower pH than other locations on the individual teeth.

3. The system of claim 1, wherein a combination of the resting pH, the minimum pH, and the pH recovery rate is utilized to determine the one or more locations on the individual teeth likely to develop demineralization.

4. The system of claim 1, wherein a combination of parameters including at least the resting pH, the minimum pH, and the pH recovery rate is provided to a machine learning algorithm that classifies caries to determine the one or more locations on the individual teeth likely to develop demineralization, and wherein the machine learning algorithm includes at least one of linear regression, multi-class classification, or a deep neural network.

5. The system of claim 1, wherein the controller further includes logic that when executed by the controller, causes the system to perform operations including:
mapping the one or more locations on a model of the individual teeth.

6. The system of claim 5, further comprising an image sensor coupled to the controller, wherein the controller further includes logic that when executed by the controller, causes the system to perform operations including:
capturing images of the individual teeth with the image sensor to generate the model; and
mapping the intensity of the florescence light emitted from the individual teeth onto the images of the individual teeth.

7. The system of claim 5, wherein the image sensor is included in the detector, and wherein a filter blocks a portion of the excitation light from reaching the detector.

8. The system of claim 1, wherein the excitation light includes 405 nm wavelength light, and wherein the florescence light includes at least one of 620 nm wavelength light or 635 nm wavelength light, and wherein the detector includes a spectrometer or two detectors, wherein the two detectors include a first detector to detect the 620 nm wavelength light and a second detector to detect the 635 nm wavelength light.

9. The system of claim 1, wherein the light emitter, the detector, and the controller are disposed in a housing, and wherein the system further includes a solution reservoir disposed within the housing and positioned to spray a sugar solution on the individual teeth.

10. The system of claim 1, wherein the pH-sensitive compound includes at least one of porphyrins or dye molecules.

11. The system of claim 1, wherein the performing the series of measurements over the period of time includes:
monitoring the one or more locations of the individual teeth likely to develop demineralization over the period of time;
repeatedly measuring the intensity of the florescence light over the period of time to determine a change in local pH of hot spots corresponding to the one or more locations of the individual teeth of the individual teeth; and
determining, based on the change in the local pH of the hot spots, whether the one or more locations of the individual teeth are likely to develop demineralization.

12. The system of claim 1, wherein the excitation light output by the light emitter has a spot size smaller than the individual teeth.

13. A method for optical detection of pH, comprising:
emitting an excitation light from a light emitter;
detecting, with a detector in response to the excitation light, florescence light produced by a pH-sensitive compound when the pH-sensitive compound contacts one or more surfaces of individual teeth;
performing a series of measurements over a period of time, each measurement included in the series of measurements measuring, using a controller coupled to the detector and the light emitter, an intensity of the florescence light emitted from the pH-sensitive compound when the pH-sensitive compound contacts the one or more surfaces of the individual teeth;
correlating the intensity of the florescence light to a pH proximate to the one or more surfaces of the individual teeth for the series of measurements to determine at least one of a resting pH, a minimum pH, or a pH recovery rate proximate to the one or more surfaces of the individual teeth; and
determining, based on at least one of the intensity of the florescence light, the resting pH, the minimum pH, or the pH recovery rate, one or more locations on the individual teeth likely to develop demineralization.

14. The method of claim 13, wherein a combination of parameters including at least the resting pH, the minimum pH, and the pH recovery rate is provided to a machine learning algorithm that classifies caries to determine the one or more locations on the individual teeth likely to develop demineralization, wherein the machine learning algorithm includes at least one of linear regression, multi-class classification, or a deep neural network.

15. The method of claim 13, wherein a combination of the resting pH, the minimum pH, and the pH recovery rate is utilized to determine the one or more locations on the individual teeth likely to develop demineralization.

16. The method of claim 13, further comprising administering a sugar solution to a mouth of a patient prior to detecting the florescence light.

17. The method of claim 13, wherein the pH-sensitive compound includes at least one of porphyrins or dye molecules.

18. The method of claim 13, further comprising mapping the intensity of the florescence light emitted from the one or more surfaces to a model of the individual teeth; and
capturing images of the individual teeth to generate the model using an image sensor coupled to the controller.

19. The method of claim 18, wherein images of the individual teeth include a 3D reconstruction of the individual teeth.

20. The method of claim 13, further comprising filtering the excitation light from the florescence light prior to receiving the florescence light with the detector.

21. The method of claim 13, wherein emitting the excitation light from the light emitter is in response to a patient pressing a button on a housing, wherein the housing includes the light emitter, the detector, and the controller.

22. The method of claim 13, wherein the one or more locations on the individual teeth likely to develop demineralization have a lower pH than other locations on the individual teeth.

23. The method of claim 13, wherein measuring the intensity of the florescence light includes at least one of an intensity ratio based measurement or a lifetime based measurement.

* * * * *